US008556880B2

(12) United States Patent
Freyman et al.

(10) Patent No.: US 8,556,880 B2
(45) Date of Patent: Oct. 15, 2013

(54) METHODS AND DEVICES FOR LOCAL THERAPEUTIC AGENT DELIVERY TO HEART VALVES

(75) Inventors: Toby Freyman, Waltham, MA (US); Tim Mickley, Corcoran, MN (US); Ruth Cheng, Watertown, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 538 days.

(21) Appl. No.: 12/205,341

(22) Filed: Sep. 5, 2008

(65) Prior Publication Data

US 2009/0069789 A1 Mar. 12, 2009

Related U.S. Application Data

(60) Provisional application No. 60/970,464, filed on Sep. 6, 2007.

(51) Int. Cl.
*A61M 31/00* (2006.01)

(52) U.S. Cl.
USPC ........................................ 604/509; 604/96.01

(58) Field of Classification Search
USPC ................. 604/509, 258, 523, 103.01, 508; 514/450, 449, 460, 427, 307
See application file for complete search history.

(56) References Cited

U.S. PATENT DOCUMENTS

| 4,531,936 A | 7/1985 | Gordon | 604/49 |
| 4,950,239 A | 8/1990 | Gahara et al. | 604/96.01 |
| 5,270,086 A | 12/1993 | Hamlin | 428/35.2 |
| 5,290,306 A | 3/1994 | Trotta et al. | 606/194 |
| 5,336,178 A | 8/1994 | Kaplan et al. | 604/509 |
| 5,500,180 A | 3/1996 | Anderson et al. | 264/532 |
| 5,512,051 A | 4/1996 | Wang et al. | 604/103.14 |
| 5,587,125 A | 12/1996 | Roychowdhury | 264/515 |
| 5,591,227 A | 1/1997 | Dinh et al. | 623/1.22 |
| 5,733,327 A | 3/1998 | Igaki et al. | 623/1.5 |
| 5,899,935 A | 5/1999 | Ding | 623/1.53 |
| 6,146,356 A | 11/2000 | Wang et al. | 604/96.01 |
| 6,364,856 B1 | 4/2002 | Ding et al. | 604/103.02 |
| 6,403,635 B1 | 6/2002 | Kinsella et al. | 514/449 |
| 6,425,881 B1 | 7/2002 | Kaesemeyer | 604/93.01 |
| 6,544,223 B1 | 4/2003 | Kokish | 604/103.01 |
| 6,572,813 B1 | 6/2003 | Zhang et al. | 264/519 |
| 6,716,242 B1 | 4/2004 | Altman | 623/1.42 |
| 6,918,929 B2 | 7/2005 | Udipi et al. | 623/1.42 |
| 6,939,376 B2 | 9/2005 | Shulze et al. | 623/1.42 |
| 7,005,097 B2 | 2/2006 | Wang et al. | 264/241 |
| 7,026,026 B2 | 4/2006 | Ferrera et al. | 428/35.2 |
| 7,112,357 B2 | 9/2006 | Miller et al. | 428/36.92 |

(Continued)

FOREIGN PATENT DOCUMENTS

| WO | WO 92/19316 | 11/1992 |
| WO | WO 96/40325 | 12/1996 |
| WO | WO 02/43796 | 6/2002 |

OTHER PUBLICATIONS

PCT International Search Report and Written Opinion, issued in International Application No. PCT/US2008/075408, dated Nov. 25, 2008.

*Primary Examiner* — Kevin C Sirmons
*Assistant Examiner* — Brandy S Lee
(74) *Attorney, Agent, or Firm* — Kenyon & Kenyon LLP

(57) ABSTRACT

Medical devices and methods for delivering a therapeutic agent to a heart valve.

6 Claims, 12 Drawing Sheets

(56) References Cited

U.S. PATENT DOCUMENTS

| | | | |
|---|---|---|---|
| 7,120,910 B2 | 10/2006 | Matsuda et al. | 24/67.5 |
| 7,387,826 B2 | 6/2008 | Burgmeier et al. | 428/35.7 |
| 7,470,252 B2 | 12/2008 | Mickley et al. | 604/103.02 |
| 2004/0133192 A1* | 7/2004 | Houser et al. | 606/14 |
| 2004/0153048 A1* | 8/2004 | Vigil et al. | 604/509 |
| 2005/0075662 A1 | 4/2005 | Pedersen et al. | 606/194 |
| 2006/0020243 A1 | 1/2006 | Speck et al. | 604/103.02 |
| 2006/0058815 A1* | 3/2006 | Mickley et al. | 606/118 |
| 2006/0229659 A1 | 10/2006 | Gifford et al. | 606/200 |
| 2007/0005011 A1 | 1/2007 | Freyman et al. | 604/102.01 |

\* cited by examiner

METHODS AND DEVICES FOR LOCAL THERAPEUTIC AGENT DELIVERY TO HEART VALVES

This application claims the benefit of priority to U.S. Provisional Patent Application Ser. No. 60/970,464, filed Sep. 6, 2007, which is hereby incorporated by reference in its entirety.

BACKGROUND OF THE INVENTION

1. Field of the Invention

The present invention relates generally to medical devices and methods of diagnosing or treating disease. More particularly, it concerns medical devices for use in delivery of therapeutic agents or diagnostic agents to cardiac valves, and methods for diagnosing or treating a disease of a cardiac valve in a subject using the same devices.

2. Description of Related Art

Valvular heart disease is a major cause of morbidity and mortality in the United States. The majority of these cases involve disorders of the aortic valve. Valvular disease of the aortic valve includes aortic stenosis, aortic regurgitation, and atresia of the aortic valve. Aortic valve stenosis results in approximately 65,000 aortic valve replacement surgeries each year in the United States.

Treatment for valvular heart disease depends on the type and severity of the diagnosis. There is no current effective treatment for individuals with minor valve problems. Those with more serious disease can be treated with therapeutic agents, such as ACE inhibitors, antiarrhythmics, antibiotics, anticoagulants, diuretics, and inotropic agents. Not uncommonly, oral therapeutic agent therapy is ineffective. Other therapeutic options are available, including mechanical dilation of the aortic valve (valvuloplasty), surgical repair of the valve, or valve replacement surgery may be needed. Each of these more invasive procedures is associated with a significant risk of complications. Patients with severe disease typically require surgical replacement of the valve. However, not all patients are treated with valve replacement, and medical therapy may be ineffective.

One of the limitations of oral therapeutic agent therapy of aortic valve disease is limited bioavailability of therapeutic agent at the site of disease (diseased valve leaflets) following oral administration. While dose of medication can be increased, such means for improving therapeutic agent delivery to the diseased valve tissue is limited because of the increased risk of toxic side effects. Various interventional methods for therapeutic agent delivery to aortic valves have been described in the literature. Generally, these devices are valvuloplasty devices. For example, U.S. Patent App. Nos. 2006/0229659 and 2005/0075662 describe valvuloplasty catheters and devices that can be designed for concurrent delivery of therapeutic agents in conjunction with valvuloplasty. The valvuloplasty procedures described therein involve the application of significant amounts of force on the aortic valve leaflets that in turn can cause restenosis of the valve or damage to the valve leaflets. Further, application of valvuloplasty with such devices carries with it a risk of significant disruption of valve function during valvuloplasty.

SUMMARY OF THE INVENTION

The present invention relates to medical devices and methods for the delivery of diagnostic or therapeutic agents to cardiac valves. Embodiments of such devices allow for administration of therapeutic agents directly to valve tissue with minimal disruption of blood flow across the valve and minimal risk of damage to valve leaflets or release of calcific nodules from valve leaflets. For example, one example device of the present invention can be used to deliver therapeutic agents to a stenotic aortic valve. Such delivery can be performed as an alternative to oral therapy, following failure of oral therapy, prior to aortic valve repair or valvuloplasty, or after aortic valve repair or valvuloplasty.

One embodiment of the present invention is a device for delivering a therapeutic agent to a heart valve that includes a body having a distal end, and a plurality of delivery members coupled to the body, where each member has a first end and a second end, and the first and seconds ends of at least one of the delivery members are coupled to the body at locations that are proximal to the distal end of the body. In some embodiments, at least one of the delivery members is at least partially coated with a therapeutic agent.

Another embodiment is a therapeutic agent delivery catheter that includes a plurality of delivery members coupled to the catheter, each having a portion positioned alongside a portion of the catheter. In some embodiments, at least one delivery member has a lumen with one or more openings to provide for a communication with that lumen such that fluid can flow out of that delivery member through the one or more openings. Any of these embodiments may optionally include at least a portion of at least one delivery member that is coated with a therapeutic agent. Lumens with one or more openings and therapeutic agent coatings are discussed in greater detail below.

Another embodiment is a device for delivering a therapeutic agent to a heart valve, including a body having a distal end and a fin longitudinally oriented along a portion of the body, the fin having a distal end located more than 1 mm from the distal end of the body, where the fin is at least partially coated with a therapeutic agent.

A further embodiment is a device for delivering a therapeutic agent to a heart valve that includes a body having a distal end, and an expandable balloon coupled to the body, the balloon having a plurality of nanofilaments, where the balloon is located more than 1 mm from the distal end of the body.

Another embodiment is a device for delivering a therapeutic agent to a heart valve that includes a body having a distal end, and an expandable balloon coupled to the body, the balloon having one or more openings such that fluid can flow out of the balloon through the one or more openings.

In more specific versions of any of these embodiments, as well as of any of those embodiments discussed in more detail below, the device can be sterilized using known techniques and sealed or otherwise enclosed in any suitable container, with our without instructions for use, which may take any suitable form.

The present invention also concerns methods of diagnosing or treating a valve disease in a subject, involving inserting one of the aforementioned devices in a blood vessel of the subject, where the device includes a delivery member, nanofilament, or fin that is at least partially coated with a therapeutic agent or diagnostic agent, and positioning the device such that the delivery member, nanofilament, or fin is in contact with a valve leaflet of the valve, where contact results in delivery of therapeutic agent or diagnostic agent to the valve and diagnosis or treatment of the valve disease in the subject. Insertion of the device can be by any method known to those of ordinary skill in the art, such as by insertion into a blood vessel of a subject followed by advancement to the proper position using radiographic guidance, by apical puncture, or by a transseptal antegrade approach.

Other embodiments pertain to methods for diagnosing or treating a valve disease in a subject, involving (a) inserting any of the aforementioned devices into a subject, where the device includes a lumen and a delivery member, fin, or balloon that has one or more openings such that fluid can flow through the one or more openings, (b) positioning the device such that the delivery member, fin, or balloon is in contact with the valve leaflets of the valve, and (c) infusing a pharmaceutical composition that includes a diagnostic agent or therapeutic agent and a carrier through the lumen of the device, wherein infusion results in release of the composition from the device and diagnosis or treatment of the valve disease. The device can be inserted into the subject using any method known to those of ordinary skill in the art. For example, in some embodiments, the device is passed over a guidewire. For example, in some embodiments, the device includes a double lumen, with one lumen configured to pass over a guidewire and a second lumen configured to allow for infusion of a fluid.

Particular embodiments of the methods are further defined as methods of treating aortic valve disease. The aortic valve disease can be any type of valve disease, such as aortic stenosis, aortic regurgitation, or atresia of the aortic valve. The devices and methods set forth herein can also be applied in the treatment of disease of the mitral and pulmonary valves.

The present invention also concerns methods of instructing another how to diagnose or treat valve disease in a subject, and embodiments of such methods include providing computer readable media comprising machine-readable instructions for showing one or more examples of how to perform diagnosis and/or treatment according to the present techniques. The techniques that are displayed can show virtual procedures or actual procedures.

Certain embodiments of the present methods pertain to methods of diagnosing a valve disease in a subject. In these embodiments, the therapeutic agent is further defined as a diagnostic agent. The method may further include detecting a signal from a diagnostic agent that is released from the device. The diagnostic agent can be any diagnostic agent known to those of ordinary skill in the art. Non-limiting examples include diatrizoate, a gadolinium chelate, and sodium fluorescein. Detecting a signal may involve use of any imaging modality known to those of ordinary skill in the art. Non-limiting examples of such modalities include PET, PET/CT, CT, SPECT, SPECT/CT, MRI, optical imaging and ultrasound.

In embodiments that concern methods of treating a valve disease in a subject, a pharmaceutically effective amount of a therapeutic agent is administered to the subject using the therapeutic agent delivery devices of the present invention. The therapeutic agent can be any therapeutic agent that is known or suspected to be of benefit in the treatment or prevention of valve disease in a subject. Non-limiting examples of such therapeutic agents include rapamycin, paclitaxel, sirolimus, statins, angiotensin converting enzyme (ACE) inhibitors, PPAR agonists, anti-inflammatory agents, anti-stenotic agents, antibiotic agents, atorvastatin, quinapril, and nitric oxide-enhancing agents.

Any embodiment of any of the present devices and methods may consist of or consist essentially of—rather than comprise—the described features and steps.

BRIEF DESCRIPTION OF THE DRAWINGS

FIG. 1B shows solid body on cross-section. FIG. 1C shows a further embodiment with hollow body, as shown on cross-section.

FIG. 11A shows that distal end of device is located within left ventricle, and drug delivery members are in contact with aortic valve leaflets. FIG. 11B depicts a magnified cross-sectional view from the lumen of the ascending aorta looking down onto the aortic valve when the valve leaflets are in the closed position following positioning of the device, showing contact of aortic valve leaflets with drug delivery members. Delivery members are coated with a therapeutic agent, and release is facilitated by contact with delivery members.

FIG. 12A shows that distal end of device is located within left ventricle, and drug delivery members are in contact with aortic valve leaflets. FIG. 12B depicts a magnified cross-sectional view from the lumen of the ascending aorta looking down onto the aortic valve when the valve leaflets are in the closed position following positioning of the device, showing contact of aortic valve leaflets with drug delivery members. Pharmaceutical composition infused through lumen of device passes through openings of delivery members.

FIG. 13A shows that the distal end of the device is located within the left ventricle, and fins are in contact with aortic valve leaflets. FIG. 13B depicts a magnified cross-sectional view from the lumen of the ascending aorta looking down onto the aortic valve when the valve leaflets are in the closed position following positioning of the device, showing positioning of fins of the device within commissures of aortic valve leaflets.

DESCRIPTION OF ILLUSTRATIVE EMBODIMENTS

The terms "comprise" (and any form of comprise, such as "comprises" and "comprising"), "have" (and any form of have, such as "has" and "having"), "include" (and any form of include, such as "includes" and "including"), and "contain" (or any other form of contain, such as "contains" and "containing") are open-ended linking verbs. Thus, a medical device for delivering a therapeutic agent to a heart valve "comprising" a body having a distal end and a plurality of delivery members coupled to the body, is a medical device possessing a body having a distal end and a plurality of delivery members coupled to the body, but is not limited to possessing only the described body and delivery members.

The terms "a" and "an" mean one or more than one. The term "another" means at least a second or more.

All numeric values are herein assumed to be modified by the term "about", whether or not explicitly indicated. The term "about" generally refers to a range of numbers that one of skill in the art would consider equivalent to the recited value, i.e., having the same function or result. In many instances, the term "about" may include numbers that are rounded to the nearest significant figure.

It will also be clear to those of ordinary skill in the art that substitutions, modifications, additions and/or rearrangements of the features of the inventive devices and methods may be made without deviating from their scope, which is defined by the claims and their equivalents. The appended claims are not to be interpreted as including means-plus-function limitations, unless such a limitation is explicitly recited in a given claim using the phrase(s) "means for" and/or "step for."

A. DEVICES

Figures 1A, 1B, 1C:
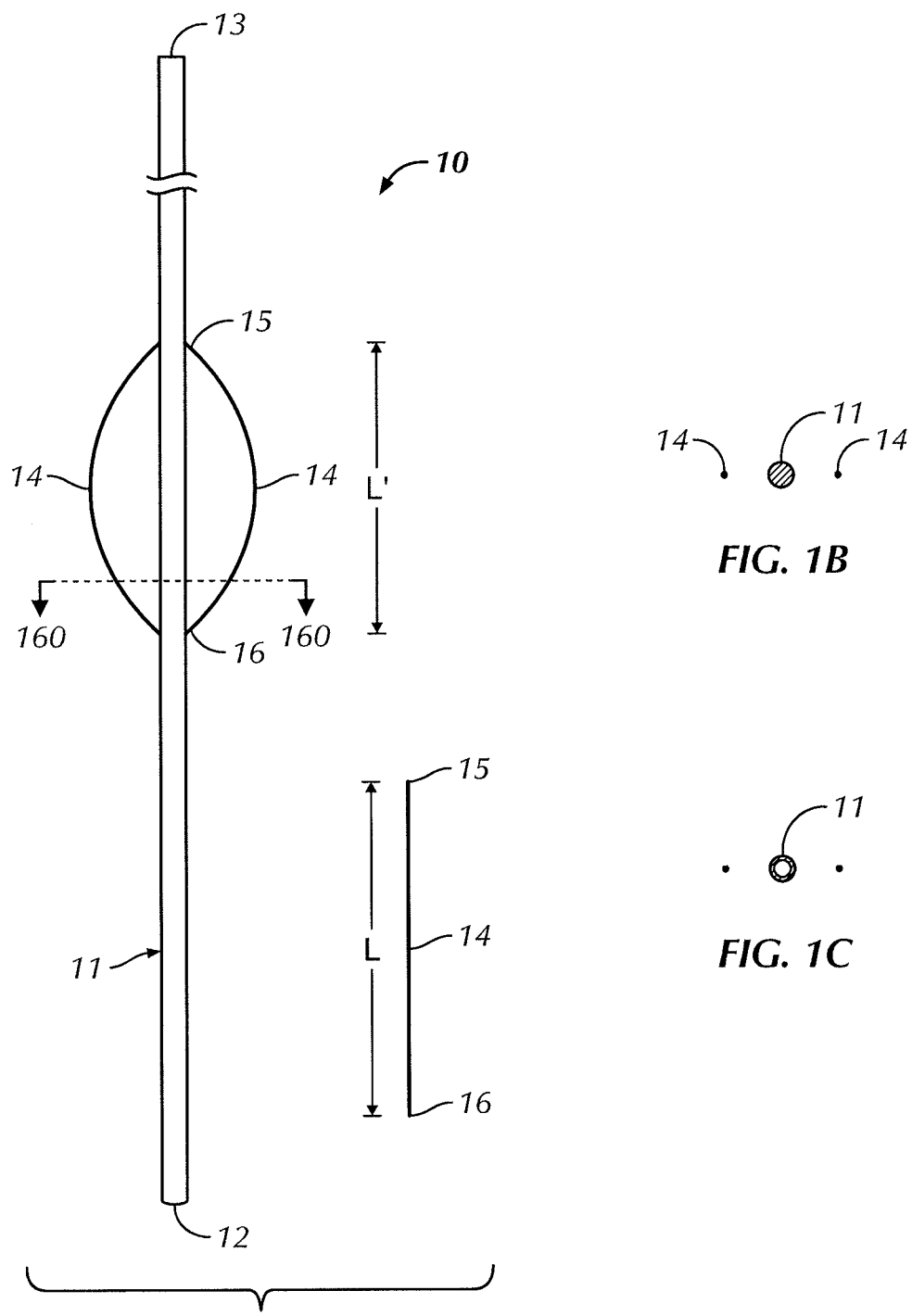
FIGS. 1A-C: a side view (FIG. 1A) and a cross-sectional view (FIG. 1B) of one of the present medical devices, showing a body having a distal end, and two drug delivery members coupled to the body at locations that are proximal to the distal end of the body. The cross-sectional view (FIG. 1B) is taken along cross-sectional line 160-160 in FIG. 1A.

One of the present medical devices is shown in FIG. 1A-B. FIG. 1A shows that medical device 10 includes body 11 having distal end 12 and proximal end 13, and a plurality of delivery members 14 coupled to body 11, where each member has first end 15 and second end 16, and first and second ends of at least one delivery member are coupled to body 11 at locations that are proximal to distal end 12 of body 11.

The device 10 may have various lengths between the distal end 12 and proximal end 13. In one embodiment, the length between distal end 12 and proximal end 13 would be sufficient to allow device 10 to be percutaneously implanted through a subject's vasculature to position the distal end 12 at a predetermined location. In one example the predetermined location is within the left ventricle of the heart of a human. As will be appreciated, the length between distal end 12 and proximal end 13 will be dependent upon each subject's physiological structure and the predetermined location within the subject. By way of example only, the length between distal end 12 and proximal end 13 could be about 10 cm to about 200 cm. In more particular embodiments, the length between distal end 12 and proximal end 13 is about 70 to about 150 cm. In even more particular embodiments, the length between distal end 12 and proximal end 13 is about 80 cm to about 120 cm.

FIG. 1B shows a cross-section of device 10 along line 160-160 of FIG. 1A. As can be seen, body 11 and delivery members 14 are solid. The material or materials chosen for delivery members 14 (discussed below) may render them flexible in some embodiments and rigid in others. In some embodiments, the body 11 of the device has a lumen, wherein the distal end 12 is open or closed (see cross-section shown in FIG. 1C).

Body 11 may be of uniform diameter, or in other embodiments may be tapered along its length such that distal end 12 has a cross-sectional diameter that is less than the cross-sectional diameter of proximal end 13. Similarly, delivery members 14 may be tapered along their length, or may be of uniform cross-sectional diameter along their length. The delivery members may be of any length L (see FIG. 1A) and have any diameter that enables them to release a therapeutic agent when positioned in proximity to a valve. As shown in FIG. 11B, delivery members are configured such that they are in contact with a valve leaflet of a heart of a subject when the body of the device is passed across a valve of the heart when the valve leaflets are in a closed or substantially closed position. In some embodiments, the delivery members are about 1 mm to about 15 cm in length. In further embodiments, they are about 1 cm to about 20 cm in length. In still further embodiments, they are about 3 cm to about 8 cm in length.

Figures 2A, 2B:
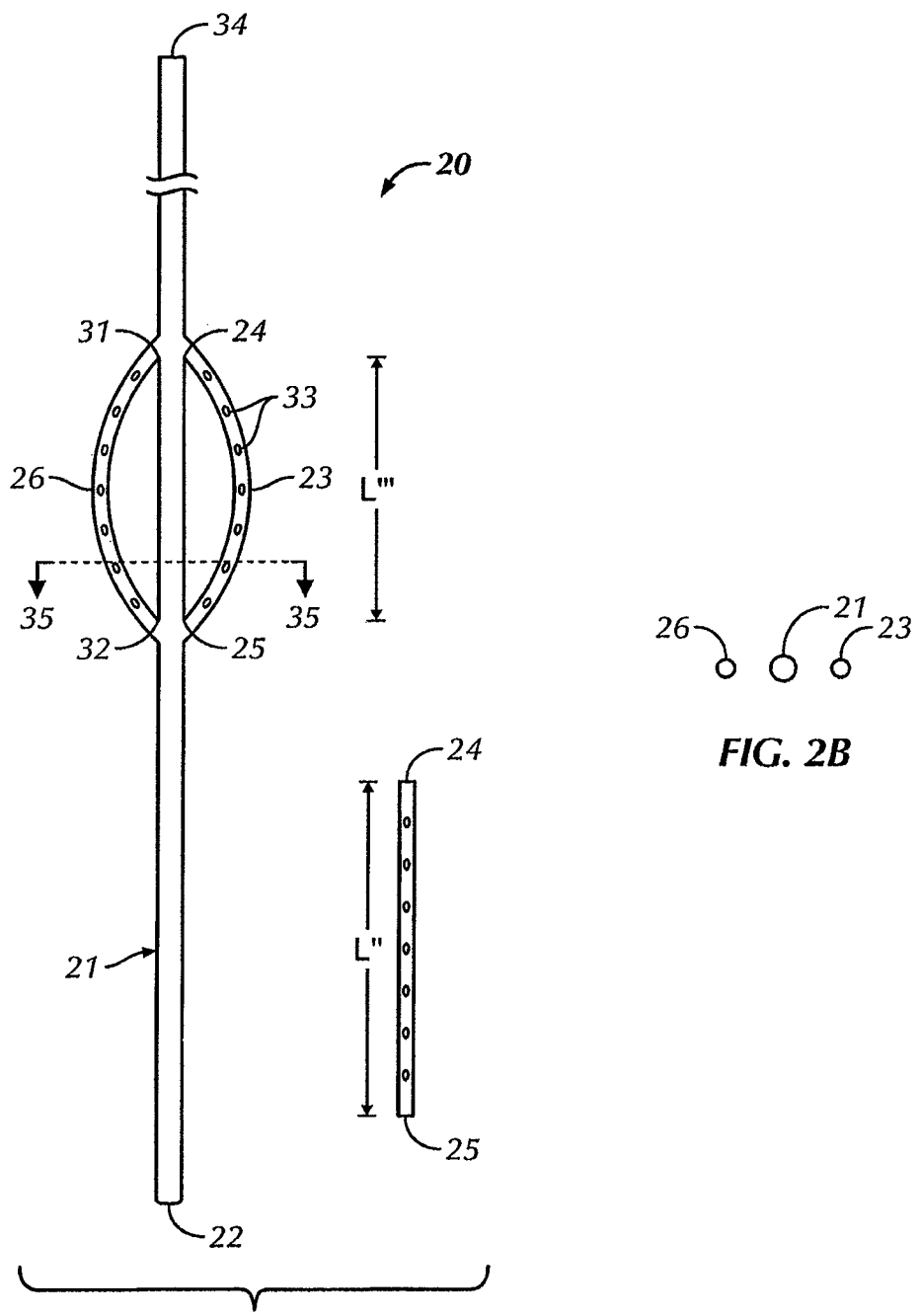
FIGS. 2A-B: a side view (FIG. 2A) and a cross-sectional view (FIG. 2B) of one of the present medical devices, showing a body having a distal end, and two drug delivery members coupled to the body, where the delivery members have a plurality of openings such that fluid can flow out of the delivery member through the one or more openings. The cross-sectional view (FIG. 2B) is taken along cross-sectional line 35-35 in FIG. 2A.

FIG. 2A shows side view of medical device 20 of the present invention. Medical device 20 includes body 21 having distal end 22 and delivery members 23 and 26. Delivery member 23 has first end 24 coupled to body 21 and second end 25 coupled to body 21. Delivery member 26 has first end 31 coupled to body 21 and second end 32 coupled to body 21. In device 20, the first ends of the delivery members are coupled to body 21 at sites that are approximately (which may include precisely) equidistant from distal end 22; the same is true of the coupling sites of the second ends with respect to each other. In further embodiments, however, the coupling sites of the first ends of the delivery members are not equidistant (e.g., they may be staggered) from distal end 22, nor are the coupling sites of the second ends.

FIG. 2B shows cross-sectional view of device 20 along line 35-35 in FIG. 2A. Device 20 includes a body 21 that is hollow. More particularly, device 20 includes body 21 that has a lumen along its length. Further, delivery members 23 and 26 are also hollow as depicted in FIG. 2B. More particularly, device 20 includes delivery members 23 and 26 that each have a lumen along their respective lengths, where each lumen of delivery members 23 and 26 is in direct communication with lumen of body 21 of device 20. In other embodiments, some delivery members have a lumen whereas other delivery members do not have a lumen. In some embodiments, less than all of the delivery members have a lumen. Of those delivery members with a lumen, the lumen of the delivery members may or may not be in communication with a lumen of the body of the device.

Device 20 includes distal end 22 of body 21 that is closed, thus preventing distal end egress of any fluid infused into an open end that is proximal to distal end 22. In further embodiments, distal end is open such that fluid can pass from lumen of body 21 through distal end 22.

Delivery members 23 and 26 include multiple openings 33. Openings 33 are in communication with lumen of delivery member 23 such that fluid can flow out of delivery member 23 through the openings 33. Thus, some embodiments of the devices of the present invention, such as device 10, include no openings in delivery members 14, whereas in other embodiments, the delivery members include one or more openings in communication with a lumen of the respective delivery member such that fluid can flow out of that delivery member through the one or more openings. Thus, for example, in device 20, infusion of fluid through open proximal end 34 passes through lumen of body 21, through lumen of delivery members 23 and 26, and out of delivery members through openings 33. In some embodiments, such as device 20, each delivery member has a lumen and one or more openings in communication with that lumen such that fluid can flow out of that delivery member through the one or more openings. In other embodiments, only some of the delivery members with a lumen have one or more openings in communication with that lumen such that fluid can flow out of the delivery member through the one or more openings.

The devices of the present invention can include any number of delivery members, so long as there are at least two delivery members. For example, in some embodiments the devices include 2 to 500 delivery members. In further embodiments, the device includes 10 to 200 delivery members. In still further embodiments, the device includes 30 to 60 delivery members. Devices 10 and 20 as discussed above each include two delivery members.

Figures 3A, 3B:
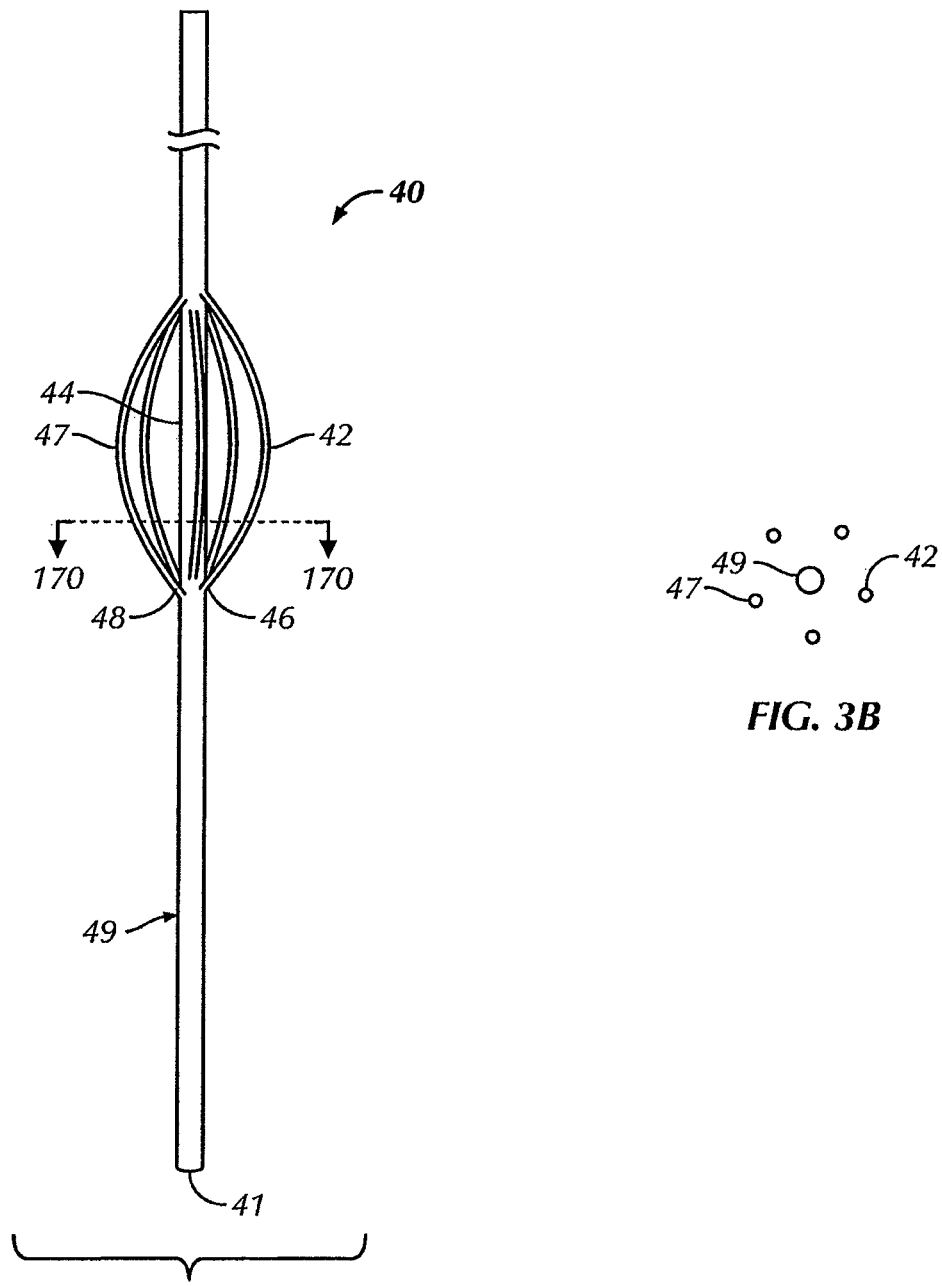
FIGS. 3A-B: a side view (FIG. 3A) and a cross-sectional view (FIG. 3A) of one of the present medical devices, showing a body having a distal end, and five drug delivery members coupled to the body. The cross-sectional view (FIG. 3B) is taken along cross-sectional line 170-170 in FIG. 3A.

FIG. 3A shows side view of device 40. Device 40 includes 5 delivery members. FIG. 3B shows cross-sectional view of device 40 along line 170-170 of FIG. 3A. Device 50 depicted in FIGS. 4A-B and device 60 depicted in FIGS. 5A-B each include 40 delivery members.

In the embodiments of the devices shown in FIGS. 1A, 2A, 3A, 4A, and 5A, the first and second ends of each of the delivery members are coupled to the body at locations that are proximal to the distal end of the body. In other embodiments, not all of the first and second ends of the delivery members are both coupled to the body. Some embodiments of the devices include delivery members where only one end of the delivery member is coupled to the body of the device. Further embodiments include some delivery members that are coupled to the distal end of the body.

Figures 4A, 4B:
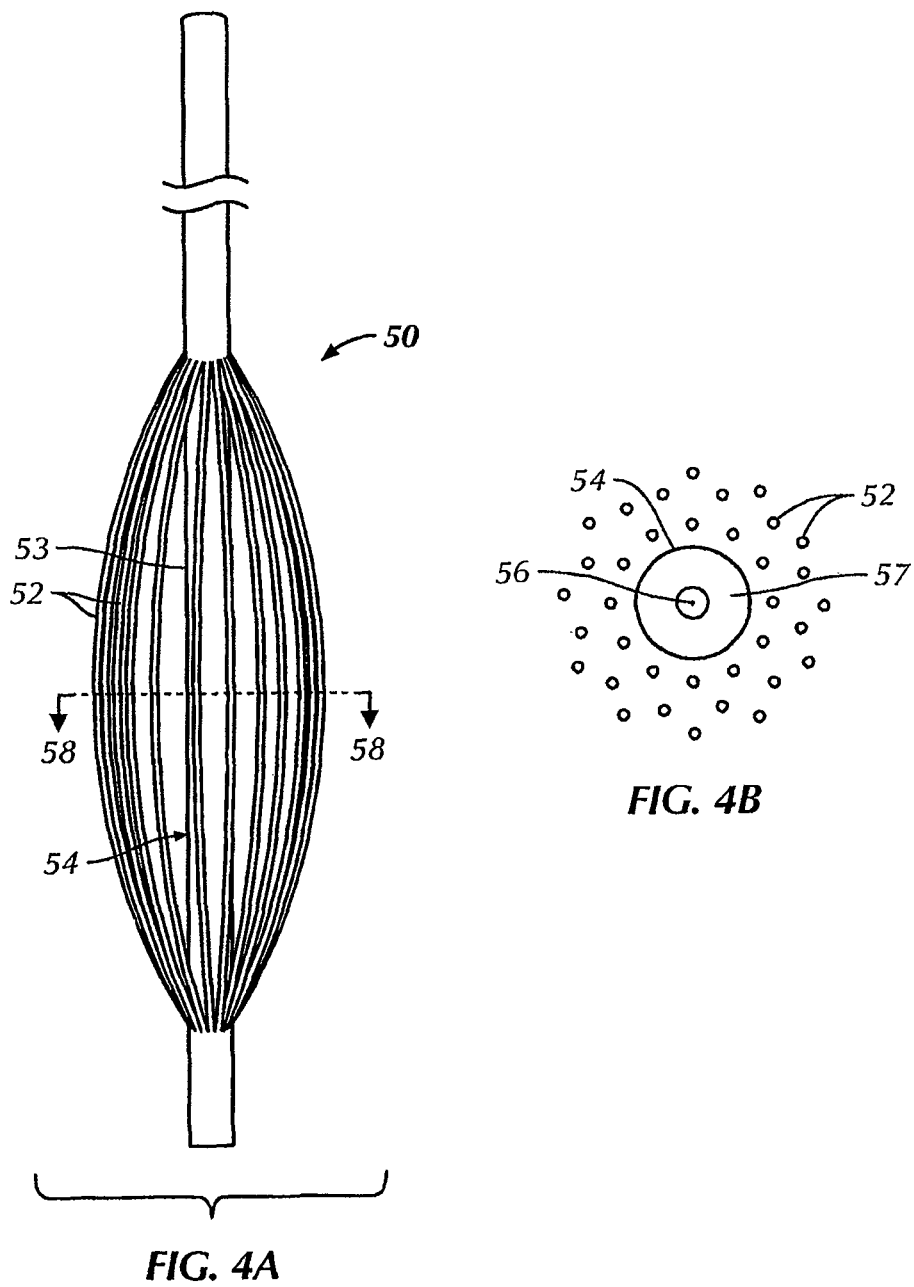
FIGS. 4A-B: a side view (FIG. 4A) and a cross-sectional view (FIG. 4B) of one of the present medical devices, showing a body having a distal end, and drug delivery members coupled to the body of the device. The delivery members have a central lumen and a plurality of openings such that fluid can flow out of the delivery members. The body of the device has a central lumen for passage of a guide wire, and a surrounding annular lumen for infusion of fluid, such as a pharmaceutical composition. The cross-sectional view (FIG. 4B) is taken along cross-sectional line 58-58 in FIG. 4A.
Figure 5A:
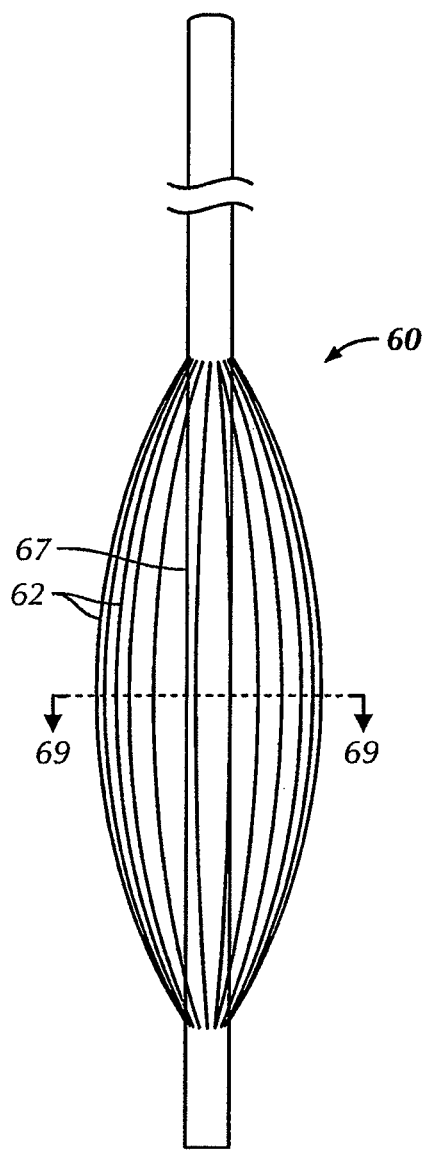
FIGS. 5A-B: a side view (FIG. 5A) and a cross-sectional view (FIG. 5B) of one of the present medical devices, showing a body having a distal end, and delivery members that are coated with a therapeutic agent. The cross-sectional view (FIG. 5B) is taken along cross-sectional line 69-69 in FIG. 5A.
Figure 5B:
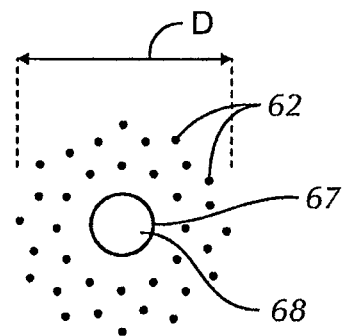

In some embodiments, such as device 50, the body 54 has a lumen that is divided along its length such that the device effectively has more than one lumen extending along its length. This is depicted in FIG. 4B, which shows a cross section of device 50 along line 58-58 of FIG. 4A. Inner lumen 56, for example, may be used for passage of a guide wire for positioning of the device, whereas outer lumen 57 may be utilized for infusion of a pharmaceutical fluid containing a therapeutic agent, as discussed in greater detail below. FIG. 5B depicts a cross-section of device 60 along line 69-69 of FIG. 5A. Inner lumen 68 is shown in FIG. 5B. Cross-sectional diameter D may be about 0.5 cm to about 2.5 cm.

In some embodiments, such as device 10, first ends 15 of delivery members 14 are coupled to body 11 at sites that are equidistant from distal end 12 of device 10, and second ends 16 of delivery members 14 are coupled to body 11 of device 10 at sites that are equidistant from distal end 12 of device 10. Other embodiments, such as device 40, the coupling sites of a group of first ends are not equidistant from the distal end of the body. For example, the distance between distal end 41 and second end 46 of delivery member 42 is greater than the distance between distal end 41 and second end 48 of delivery member 47. Thus, in some embodiments, the shortest distance between the distal end of the body (e.g., distal end 41) and the distal-most coupling location of a delivery member to the body (e.g., the coupling location of second end 48 to the body) is between about 0.2 cm to about 20 cm. In further embodiments, the shortest distance between the distal end of the body and the distal-most coupling location of a delivery member to the body is between about 1 cm to about 15 cm. In more particular embodiments, the shortest distance between the distal end of the body and the distal-most coupling location of a delivery member to the body is between about 3 cm to about 10 cm. As discussed in greater detail below, the distance between the distal end of the body and the distal-most coupling location of a delivery member to the body is selected largely based on subject-specific parameters, such as the nature of the subject and the size of the left ventricle. For example, as discussed in greater detail below, the distal end of the device is positioned in the left ventricle, and the delivery members are configured in a manner such that contact between the aortic valve leaflets and the delivery members occurs when the distal end of the device is positioned in the left ventricle.

Device 10 includes delivery members 14 where length L of delivery member 14 is less than twice L', the distance between the site of coupling of first end 15 of delivery member 14 and second end 16 of delivery member 14 to body 11. Device 20 includes delivery member 23 where length L" of delivery member 23 is less than twice L'", the shortest distance between the site of coupling of first end 24 and second end 25 of delivery member 23 to body of device 21. Thus, in some embodiments, the length of any delivery member is less than twice the shortest distance between the site of coupling of the first end and send end of that delivery member to the body of the device. In more particular embodiments, the length of all delivery members is less than twice the shortest distance between the site of coupling of the first end and send end of any delivery member to the body of the device. Thus, in some embodiments of the devices set forth in this application, at least one delivery member is located alongside the body of the delivery device.

In embodiments of the present invention, the device may include at least one delivery member that is at least partially coated with a therapeutic agent. In some embodiments, at least a portion of all delivery members is coated with a therapeutic agent. In further embodiments, at least one delivery member of the device is entirely coated with a therapeutic agent. In more particular embodiments, all delivery members of a device are coated with a therapeutic agent. A therapeutic agent may include a mixture of two or more substances, such as a mixture of therapeutic agents.

Coating of a delivery device can be by any method known to those of ordinary skill in the art. The device may be dipped, sprayed or painted with a composition containing a therapeutic agent. In some embodiments, the therapeutic agent is incorporated into intentionally created surface irregularities or specific surface features such as divots or holes. In some embodiments, an initial polymer/solvent mixture can be formed and then the therapeutic agent added to the polymer/solvent mixture. Alternatively, the polymer, solvent, and therapeutic agent can be added simultaneously to form the mixture. The polymer/solvent/therapeutic agent mixture may be a dispersion, suspension or a solution. The therapeutic agent may also be mixed with the polymer in the absence of a solvent. The therapeutic agent may be dissolved in the polymer/solvent mixture or in the polymer to be in a true solution with the mixture or polymer, dispersed into fine or micronized particles in the mixture or polymer, suspended in the mixture or polymer based on its solubility profile, or combined with micelle-forming compounds such as surfactants or adsorbed onto small carrier particles to create a suspension in the mixture or polymer. The coating may comprise multiple polymers and/or multiple therapeutic agents.

In some embodiments, a biodegradable therapeutic agent-polymer coating known to those skilled in the art may be used. Exemplary methods of using such polymers or delivery systems are also provided by U.S. Pat. Nos. 5,591,227; 5,733,327; 5,899,935; 6,364,856; 6,403,635; 6,425,881; 6,716,242; 6,918,929; and 6,939,376, each of which is incorporated herein by reference in its entirety. Any of the above mentioned therapeutic agents may be incorporated into a polymeric coating.

The polymers of the polymeric coatings may be biodegradable or non-biodegradable. Non-limiting examples of suitable non-biodegradable polymers include polystyrene; polyisobutylene copolymers and styrene-isobutylene-styrene block copolymers such as styrene-isobutylene-styrene tert-block copolymers (SIBS); polyvinylpyrrolidone including cross-linked polyvinylpyrrolidone; polyvinyl alcohols, copolymers of vinyl monomers such as EVA; polyvinyl ethers; polyvinyl aromatics; polyethylene oxides; polyesters including polyethylene terephthalate; polyamides; polyacrylamides; polyethers including polyether sulfone; polyalkylenes including polypropylene, polyethylene and high molecular weight polyethylene; polyurethanes; polycarbonates, silicones; siloxane polymers; cellulosic polymers such as cellulose acetate; polymer dispersions such as polyurethane dispersions (BAYHDROL®); squalene emulsions; and mixtures and copolymers of any of the foregoing.

Non-limiting examples of suitable biodegradable polymers include polycarboxylic acid, polyanhydrides including maleic anhydride polymers; polyorthoesters; poly-amino acids; polyethylene oxide; polyphosphazenes; polylactic acid, polyglycolic acid and copolymers and mixtures thereof such as poly(L-lactic acid)(PLLA), poly(D,L,-lactide), poly (lactic acid-co-glycolic acid), 50/50 (DL-lactide-co-glycolide); polydioxanone; polypropylene fumarate; polydepsipeptides; polycaprolactone and co-polymers and mixtures thereof such as poly(D,L-lactide-co-caprolactone) and polycaprolactone co-butylacrylate; polyhydroxybutyrate valerate and blends; polycarbonates such as tyrosine-derived polycarbonates and arylates, polyiminocarbonates, and polydimethyltrimethylcarbonates; cyanoacrylate; calcium phosphates; polyglycosaminoglycans; macromolecules such as polysaccharides (including hyaluronic acid; cellulose, and hydroxypropylmethyl cellulose; gelatin; starches; dextrans; alginates and derivatives thereof), proteins and polypeptides; and mixtures and copolymers of any of the foregoing. The biodegradable polymer may also be a surface erodable polymer such as polyhydroxybutyrate and its copolymers, polycaprolactone, polyanhydrides (both crystalline and amorphous), maleic anhydride copolymers, and zinc-calcium phosphate.

In some embodiments, coating of the device involves use of an adhesive. Examples of adhesives include acrylates, such as cyanoacrylate, methacrylates, alkyl acrylates, hydrocolloids, hydrogels, polyisobutylene, and adhesives that are based on a gel matrix, such as polyacrylic acid-based gel matrix adhesives.

In some embodiments, the coating which will allow for controlled release of the therapeutic agent. The composition that is coated onto the device may have one or more additional components, such as biodegradable polymers described above, a physiologically acceptable adhesive, proteins, polysaccharides or the like.

The therapeutic agent that is coated can be any therapeutic agent known to those of ordinary skill in the art. A "therapeutic agent" is defined herein to refer to a substance used in the diagnosis, treatment, or prevention of a disease. Any therapeutic agent known to those of ordinary skill in the art to be of benefit in the diagnosis, treatment or prevention of disease of a heart or heart valve is contemplated as a therapeutic agent in the context of the present invention. The therapeutic agent may be any pharmaceutically acceptable agent such as a non-genetic therapeutic agent, a biomolecule, a small molecule, or cells. Any of the therapeutic agents may be combined to the extent such combination is biologically compatible.

In particular embodiments, the therapeutic agent is sirolimus, zotavolimus, paclitaxel, rapamycin, or a nitric oxide-enhancing agent.

Exemplary non-genetic therapeutic agents include anti-angiogenic agents (e.g., bevacizumab), nitroglycerin, isosorbide mononitrate, nitronaproxen, nitroflurbiprofen, nitric oxide, nitric oxide mimetics, anti-thrombogenic agents such heparin, heparin derivatives, prostaglandin (including micellar prostaglandin E1), urokinase, and PPack (dextrophenylalanine proline arginine chloromethylketone); anti-proliferative agents such as enoxaprin, angiopeptin, sirolimus (rapamycin), tacrolimus, everolimus, monoclonal antibodies capable of blocking smooth muscle cell proliferation, hirudin, and acetylsalicylic acid; anti-inflammatory agents such as dexamethasone, rosiglitazone, prednisolone, corticosterone, budesonide, estrogen, estrodiol, sulfasalazine, fenfibrate, provastatin, simvastatin, proglitazone, acetylsalicylic acid, mycophenolic acid, and mesalamine; anti-neoplastic/anti-proliferative/anti-mitotic agents such as paclitaxel, epothilone, cladribine, 5-fluorouracil, methotrexate, doxorubicin, daunorubicin, cyclosporine, cisplatin, vinblastine, vincristine, epothilones, endostatin, trapidil, halofuginone, and angiostatin; anti-cancer agents such as antisense inhibitors of c-myc oncogene; anti-microbial agents such as triclosan, cephalosporins, aminoglycosides, nitrofurantoin, silver ions, compounds, or salts; biofilm synthesis inhibitors such as non-steroidal anti-inflammatory agents and chelating or decalcifying agents such as ethylenediaminetetraacetic acid, O,O'- bis(2-aminoethyl)ethyleneglycol-N,N,N',N'-tetraacetic acid, nitric acid, formic acid, EDTA, citric acid, and mixtures thereof; antibiotics such as gentamycin, rifampin, minocyclin, and ciprofolxacin; antibodies including chimeric antibodies and antibody fragments; ropivacaine; nitric oxide; nitric oxide (NO) donors such as lisidomine, molsidomine, L-arginine, NO-carbohydrate adducts, polymeric or oligomeric NO adducts; vascular cell growth promotors such as growth factors, transcriptional activators, and translational promotors; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; inhibitors of heat shock proteins such as geldanamycin; angiotensin converting enzyme (ACE) inhibitors; beta-blockers; bAR kinase (bARKct) inhibitors; phospholamban inhibitors; and any combinations and prodrugs of the above.

Exemplary biomolecules include peptides, polypeptides and proteins; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Nucleic acids may be incorporated into delivery systems such as, for example, vectors (including viral vectors), plasmids or liposomes.

Non-limiting examples of proteins include serca-2 protein, osteopontin, monocyte chemoattractant proteins ("MCP-1) and bone morphogenic proteins ("BMP's"), such as, for example, BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15. Preferred BMPS are any of BMP-2, BMP-3, BMP-4, BMP-5, BMP-6, and BMP-7. These BMPs can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them. Non-limiting examples of genes include survival genes that protect against cell death, such as anti-apoptotic Bcl-2 family factors and Akt kinase; serca 2 gene; and combinations thereof. Non-limiting examples of angiogenic factors include acidic and basic fibroblast growth factors, vascular endothelial growth factor, epidermal growth factor, transforming growth factor .alpha. and .beta., platelet-derived endothelial growth factor, platelet-derived growth factor, tumor necrosis factor .alpha., hepatocyte growth factor, and insulin like growth factor. A non-limiting example of a cell cycle inhibitor is a cathespin D (CD) inhibitor. Non-limiting examples of anti-restenosis agents include p15, p16, p18, p19, p21, p27, p53, p57, Rb, nFkB and E2F decoys, thymidine kinase ("TK") and combinations thereof and other agents useful for interfering with cell proliferation. Exemplary small molecules include hormones, nucleotides, amino acids, sugars, and lipids and compounds have a molecular weight of less than 100 kD.

Exemplary cells include stem cells, progenitor cells, endothelial cells, adult cardiomyocytes, and smooth muscle cells. Cells can be of human origin (autologous or allogenic) or from an animal source (xenogenic), or genetically engineered. Non-limiting examples of cells include side population (SP) cells, lineage negative cells, mesenchymal stem cells including mesenchymal stem cells with 5-aza, cord blood cells, cardiac or other tissue derived stem cells, whole bone marrow, bone marrow mononuclear cells, endothelial progenitor cells, skeletal myoblasts or satellite cells, muscle derived cells, go cells, endothelial cells, adult cardiomyocytes, fibroblasts, smooth muscle cells, adult cardiac fibroblasts +5-aza, genetically modified cells, tissue engineered grafts, MyoD scar fibroblasts, pacing cells, embryonic stem cell clones, embryonic stem cells, fetal or neonatal cells, immunologically masked cells, and teratoma derived cells.

In certain embodiments, the therapeutic agent is an agent that aids in the removal or prevention of blood clots. Non-limiting examples of antithrombotic and/or fibrinolytic agents include anticoagulants, anticoagulant antagonists, antiplatelet agents, thrombolytic agents, thrombolytic agent antagonists or combinations thereof. Examples of antithrombotic agents include aspirin and wafarin (coumadin). Examples of anticoagulant include acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodium, oxazidione, pentosan polysulfate, phenindione, phenprocoumon, phosvitin, picotamide, tioclomarol and warfarin. Non-limiting examples of antiplatelet agents include aspirin, a dextran, dipyridamole (persantin), heparin, sulfinpyranone (anturane) and ticlopidine (ticlid). Non-limiting examples of thrombolytic agents include tissue plaminogen activator (activase), plasmin, pro-urokinase, urokinase (abbokinase) streptokinase (streptase), and anistreplase/APSAC (eminase).

In some embodiments, the therapeutic agent is a blood coagulant. Non-limiting examples of a blood coagulation promoting agent include thrombolytic agent antagonists and anticoagulant antagonists. Non-limiting examples of anticoagulant antagonists include protamine and vitamine K1.

Non-limiting examples of thrombolytic agent antagonists include amiocaproic acid (amicar) and tranexamic acid (amstat). Non-limiting examples of antithrombotics include anagrelide, argatroban, cilstazol, daltroban, defibrotide, enoxaparin, fraxiparine, indobufen, lamoparan, ozagrel, picotamide, plafibride, tedelparin, ticlopidine and triflusal.

The therapeutic agent may be an antiarrythmic agent. Non-limiting examples of antiarrythmic agents include Class I antiarrythmic agents (sodium channel blockers), Class II antiarrythmic agents (beta-adrenergic blockers), Class II antiarrythmic agents (repolarization prolonging therapeutic agents), Class IV antiarrythmic agents (calcium channel blockers) and miscellaneous antiarrythmic agents. Non-limiting examples of sodium channel blockers include Class IA, Class IB and Class IC antiarrhythmic agents. Non-limiting examples of Class IA antiarrhythmic agents include disppyramide (norpace), procainamide (pronestyl) and quinidine (quinidex). Non-limiting examples of Class IB antiarrhythmic agents include lidocaine (xylocalne), tocamide (tonocard) and mexiletine (mexitil). Non-limiting examples of Class IC antiarrhythmic agents include encamide (enkaid) and flecamide (tambocor). Non-limiting examples of a beta blocker, otherwise known as a β-adrenergic blocker, a β-adrenergic antagonist or a Class II antiarrhythmic agent, include acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In certain aspects, the beta blocker comprises an aryloxypropanolamine derivative. Non-limiting examples of aryloxypropanolamine derivatives include acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, moprolol, nadolol, nipradilol, oxprenolol, penbutolol, pindolol, propanolol, talinolol, tertatolol, timolol and toliprolol. Non-limiting examples of an agent that prolong repolarization, also known as a Class III antiarrhythmic agent, include amiodarone (cordarone) and sotalol (betapace). Non-limiting examples of a calcium channel blocker, otherwise known as a Class IV antiarrythmic agent, include an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexyline. In certain embodiments a calcium channel blocker comprises a long-acting dihydropyridine (nifedipine-type) calcium antagonist. Non-limiting examples of miscellaneous antiarrhymic agents include adenosine (adenocard), digoxin (lanoxin), acecamide, ajmaline, amoproxan, aprindine, bretylium tosylate, bunaftine, butobendine, capobenic acid, cifenline, disopyranide, hydroquinidine, indecamide, ipatropium bromide, lidocaine, lorajmine, lorcamide, meobentine, moricizine, pirmenol, prajmaline, propafenone, pyrinoline, quinidine polygalacturonate, quinidine sulfate and viquidil.

Other examples of therapeutic agents include antihypertensive agents. Non-limiting examples of antihypertensive agents include sympatholytic, alpha/beta blockers, alpha blockers, anti-angiotensin II agents, beta blockers, calcium channel blockers, vasodilators and miscellaneous antihypertensives. Non-limiting examples of an alpha blocker, also known as an α-adrenergic blocker or an α-adrenergic antagonist, include amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Non-limiting examples of quinazoline derivatives include alfuzosin, bunazosin, doxazosin, prazosin, terazosin and trimazosin. In certain embodiments, an antihypertensive agent is both an alpha and beta adrenergic antagonist. Non-limiting examples of an alpha/beta blocker comprise labetalol (normodyne, trandate). Non-limiting examples of anti-angiotension II agents include angiotensin converting enzyme inhibitors and angiotension II receptor antagonists. Non-limiting examples of angiotension converting enzyme inhibitors (ACE inhibitors) include alacepril, enalapril (vasotec), captopril, cilazapril, delapril, enalaprilat, fosinopril, lisinopril, moveltopril, perindopril, quinapril and ramipril. Non-limiting examples of an angiotensin II receptor blocker, also known as an angiotension II receptor antagonist, an ANG receptor blocker or an ANG-II type-1 receptor blocker (ARBS), include angiocandesartan, eprosartan, irbesartan, losartan and valsartan. Non-limiting examples of a sympatholytic include a centrally acting sympatholytic or a peripherially acting sympatholytic. Non-limiting examples of a centrally acting sympatholytic, also known as an central nervous system (CNS) sympatholytic, include clonidine (catapres), guanabenz (wytensin) guanfacine (tenex) and methyldopa (aldomet). Non-limiting examples of a peripherally acting sympatholytic include a ganglion blocking agent, an adrenergic neuron blocking agent, a β-adrenergic blocking agent or a alpha1-adrenergic blocking agent. Non-limiting examples of a ganglion blocking agent include mecamylamine (inversine) and trimethaphan (arfonad). Non-limiting of an adrenergic neuron blocking agent include guanethidine (ismelin) and reserpine (serpasil). Non-limiting examples of a β-adrenergic blocker include acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren). Non-limiting examples of alpha1-adrenergic blocker include prazosin (minipress), doxazocin (cardura) and terazosin (hytrin). In certain embodiments a cardiovasculator therapeutic agent may comprise a vasodilator (e.g., a cerebral vasodilator, a coronary vasodilator or a peripheral vasodilator). In certain preferred embodiments, a vasodilator comprises a coronary vasodilator. Non-limiting examples of a coronary vasodilator include amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(β-diethylaminoethyl ether), hexobendine, itramin tosylate, khellin, lidoflanine, mannitol hexanitrane, medibazine, nicorglycerin, pentaerythritol tetranitrate, pentrinitrol, perhexyline, pimethylline, trapidil, tricromyl, trimetazidine, trolnitrate phosphate and visnadine. In certain aspects, a vasodilator may comprise a chronic therapy vasodilator or a hypertensive emergency vasodilator. Non-limiting examples of a chronic therapy vasodilator include hydralazine (apresoline) and minoxidil (loniten). Non-limiting examples of a hypertensive emergency vasodilator include nitroprusside (nipride), diazoxide (hyperstat IV), hydralazine (apresoline), minoxidil (loniten) and verapamil.

Non-limiting examples of miscellaneous antihypertensives include ajmaline, γ-aminobutyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzolimine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain aspects, an antihypertensive may comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quanternary ammonium compound, a reserpine derivative or a suflonamide derivative. Non-limiting examples of arylethanolamine derivatives include amosulalol, bufuralol, dilevalol, labetalol, pronethalol, sotalol and sulfinalol. Non-limiting examples of benzothiadiazine derivatives include althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide. Non-limiting examples of N-carboxyalkyl(peptide/lactam) derivatives include alacepril, captopril, cilazapril, delapril, enalapril, enalaprilat, fosinopril, lisinopril, moveltipril, perindopril, Non-limiting examples of dihydropyridine derivatives include amlodipine, felodipine, isradipine, nicardipine, nifedipine, nilvadipine, nisoldipine and nitrendipine. Non-limiting examples of guanidine derivatives include bethanidine, debrisoquin, guanabenz, guanacline, guanadrel, guanazodine, guanethidine, guanfacine, guanochlor, guanoxabenz and guanoxan. Non-limiting examples of hydrazines/phthalazines include budralazine, cadralazine, dihydralazine, endralazine, hydracarbazine, hydralazine, pheniprazine, pildralazine and todralazine. Non-limiting examples of imidazole derivatives include clonidine, lofexidine, phentolamine, tiamenidine and tolonidine. Non-limiting examples of quanternary ammonium compounds include azamethonium bromide, chlorisondamine chloride, hexamethonium, pentacynium bis(methylsulfate), pentamethonium bromide, pentolinium tartrate, phenactropinium chloride and trimethidinium methosulfate. Non-limiting examples of reserpine derivatives include bietaserpine, deserpidine, rescinnamine, reserpine and syrosingopine. Non-limiting examples of sulfonamide derivatives include ambuside, clopamide, furosemide, indapamide, quinethazone, tripamide and xipamide.

Other examples of therapeutic agents include vasopressors. Non-limiting examples of a vasopressor, also known as an antihypotensive, include amezinium methyl sulfate, angiotensin amide, dimetofrine, dopamine, etifelmin, etilefrin, gepefrine, metaraminol, midodrine, norepinephrine, pholedrine and synephrine.

Other examples of therapeutic agents include anti-angiotension II agents, afterload-preload reduction treatment, diuretics and inotropic agents. Examples of afterload-preload reduction agents include hydralazine (apresoline) and isosorbide dinitrate (isordil, sorbitrate). Non-limiting examples of a diuretic include a thiazide or benzothiadiazine derivative (e.g., althiazide, bendroflumethazide, benzthiazide, benzylhydrochlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamphamide, mercaptomerin sodium, mercumallylic acid, mercumatilin dodium, mercurous chloride, mersalyl), a pteridine (e.g., furtherene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., acetazolamide, ambuside, azosemide, bumetanide, butazolamide, chloraminophenamide, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, tripamide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzolimine, perhexyline, ticrnafen and urea. Non-limiting examples of a positive inotropic agent, also known as a cardiotonic, include acefylline, an acetyldigitoxin, 2-amino-4-picoline, aminone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol. In particular aspects, an intropic agent is a cardiac glycoside, a beta-adrenergic agonist or a phosphodiesterase inhibitor. Non-limiting examples of a cardiac glycoside includes digoxin (lanoxin) and digitoxin (crystodigin). Non-limiting examples of a β-adrenergic agonist include albuterol, bambuterol, bitolterol, carbuterol, clenbuterol, clorprenaline, denopamine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Non-limiting examples of a phosphodiesterase inhibitor include aminone (inocor). Antianginal agents may comprise organonitrates, calcium channel blockers, beta blockers and combinations thereof. Non-limiting examples of organonitrates, also known as nitrovasodilators, include nitroglycerin (nitro-bid, nitrostat), isosorbide dinitrate (isordil, sorbitrate) and amyl nitrate (aspirol, vaporole).

In certain embodiments, the therapeutic agent is an antimicrobial agent. Examples include ampicillin, amoxicillin, penicillin, clindamycin, gentamycin, kanamycin, neomycin, natamycin, nafcillin, rifampin, tetracycline, vancomycin, bleomycin, doxycyclin, amikacin, netilmicin, streptomycin, tobramycin, loracarbef, ertapenem, imipenem, meropenem, cefadroxil, cefazolin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, teicoplanin, azithromycin, clarithromycin, dirithromycin, erythromycin, roxithromycin, troleandomycin, aztreonam, azlocillin, carbenicillin, cloxacillin, dicloxacillin, flucloxacillin, mezlocillin, piperacillin, ticarcillin, bacitracin, colistin, polymyxin b, ciprofloxacin, enoxacin, gatifloxacin, levofloxacin, lomefloxacin, moxifloxacin, norfloxacin, ofloxacin, trovafloxacin, mafenide, prontosil, sulfacetamide, sulfamethizole, sulfanilimide, sulfasalazine, sulfisoxazole, trimethoprim, trimethoprim-sulfamethoxazole, demeclocycline, minocycline, oxytetracycline, arsphenamine, chloramphenicol, ethambutol, fosfomycin, furazolidone, isoniazid, linezolid, metronidazole, mupirocin, nitrofurantoin, platensimycin, pyrazinamide, quinupristin, dalfopristin, spectinomycin, and telithromycin.

In some embodiments, the device is further defined as a delivery catheter that includes a plurality of delivery members coupled to the catheter, each having a portion positioned alongside a portion of the catheter. A "catheter" is defined as a flexible tube that can be inserted into the body. "Alongside" in the context of the present invention refers to the relative positioning of the catheter and the delivery member whereby the shortest distance between the most distal portion of the delivery member from the catheter is not greater than 5 cm when the catheter and delivery member(s) are in an unencumbered position. A delivery member having a portion that is positioned "alongside" a portion of the body means that a plane oriented perpendicular to that portion of the body (when that portion is straight) and intersecting that portion of the body also intersects the delivery member portion.

The catheter can include any number of delivery members. For example, the number of delivery members may be 2 to 500. More particular embodiments include 10 to 200 delivery members. Even more particular embodiments include 30 to 60 delivery members. In some embodiments, the catheter has a lumen. At least one of the delivery members may have a lumen. The lumen of any delivery member, for example, may be in communication with a lumen of the catheter. In particular embodiments, each delivery member has a lumen that communicates with the lumen of the catheter, such that fluid can flow from the lumen of the catheter into the lumen of any delivery member. The catheter and delivery members can be composed of any material known to those of ordinary skill in the art, as discussed in greater detail below. In some embodiments, the catheter has at least one delivery member with a lumen and one or more openings to provide for communication with that lumen such that fluid can flow out of that delivery member through the one or more openings. Delivery members will be about 10 µm to about 300 µm internal diameter, and about 0.0025 cm to about 0.5 cm outside diameter. In particular embodiments, the internal diameter of delivery members is about 0.0025 cm to about 0.025 cm. In particular embodiments, the outside diameter is about 0.0127 cm to about 0.25 cm. The body will be about 3 Fr to 10 Fr outside diameter. As discussed above, at least a portion of at least one delivery member may be coated with a therapeutic agent. Embodiments include catheters where some or all of the delivery members are at least partially coated with a therapeutic agent. Additional embodiments include catheters where some or all of the delivery members are entirely coated with a therapeutic agent. The coating may composed of any therapeutic agent known to those of ordinary skill in the art. Examples are as set forth above. In particular embodiments, the therapeutic agent is rapamycin, paclitaxel, sirolimus, or a nitric oxide-enhancing agent.

Figure 6A:
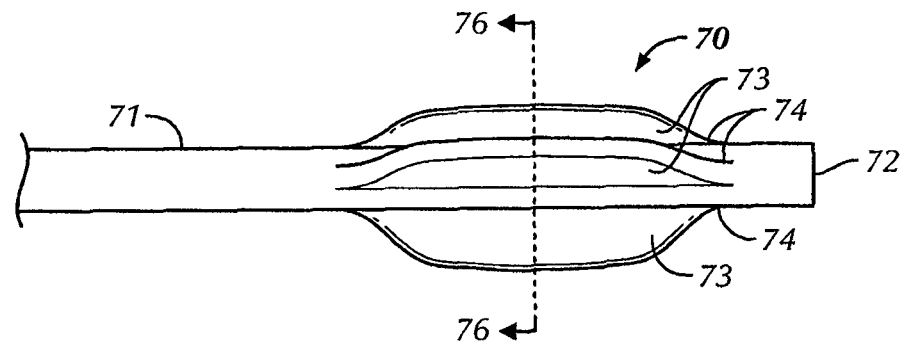
FIGS. 6A-B: a side view (FIG. 6A) and a cross-sectional view (FIG. 6B) of one of the present medical devices having a body and three fins, where the fins are coated with a therapeutic agent. The cross-sectional view (FIG. 6B) is taken along cross-sectional line 76-76 of FIG. 6A.
Figure 6B:
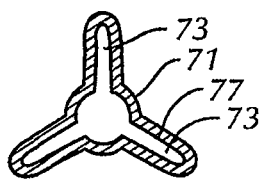

Other embodiments of the present medical devices include devices for delivering a therapeutic agent to a heart valve, including a body having a distal end and a fin at least partially covered with a therapeutic agent longitudinally oriented along a portion of the body, the fin having a distal end located more than 1 mm from the distal end of the body. One such medical device is shown in FIG. 6A-6B. FIG. 6A shows a side view of device 70. Device 70 includes body 71 having distal end 72 and three therapeutic agent-coated fins 73 longitudinally oriented along body 71. Each fin has a distal end 74 located more than 1 mm from the distal end 72 of body 71. In particular embodiments, the device includes 3 fins, configured to allow for closure of aortic valve leaflets with minimal disruption to valve function. The distal ends of the fins may be located at the same distance from distal end of body, or at different distances from the distal end of body, so long as at least one fin is located more than 1 mm from distal end of body. In particular embodiments, the distal end of each fin of the device is located between about 2 mm to about 20 cm from the distal end of body. In more particular embodiments, the distal end of each fin of the device is located between about 1 cm to about 20 cm from the distal end of body. In even more particular embodiments, the distal end of each fin of device is located between about 3 cm to about 15 cm from the distal end of the body. In further embodiments, the distal end of each fin of device is located between about 1 mm to about 5 cm from the distal end of body.

A cross-section of device 70 along a line 76-76 in FIG. 6A is shown in FIG. 6B. A coating of therapeutic agent 77 is present on fin 73. The fins of device 70 are configured to allow for contact with aortic valve leaflets of a human subject and minimal disruption of aortic valve function when device 70 is inserted into a subject and positioned such that fins 73 are in contact with valve leaflets of aortic valve. In some embodiments, one or more fins are partially coated with a therapeutic agent. In further embodiments, one or more fins are entirely coated with a therapeutic agent. Coating of a fin with a therapeutic agent can be by any method known to those of ordinary skill in the art, and is discussed in greater detail below. A fin may be partially coated with a therapeutic agent, or entirely coated with a therapeutic agent. In some embodiments, not all fins are coated with a therapeutic agent. In further embodiments, all fins are at least partially coated with a therapeutic agent. In still further embodiments, all fins are entirely coated with a therapeutic agent.

Figure 7A:
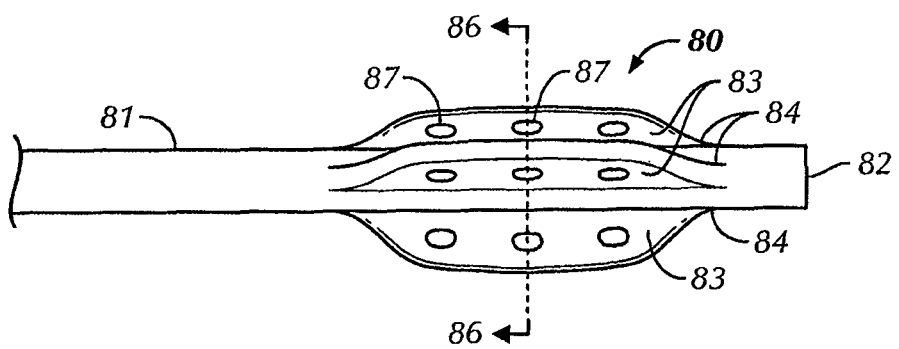
FIGS. 7A-B: a side view (FIG. 7A) and a cross-sectional view (FIG. 7B) of one of the present medical devices having a body and three fins, where the fins have a lumen that is in communication with a lumen of the body, and where each fin has a plurality of openings to allow for passage of fluid through the plurality of openings. The cross-sectional view (FIG. 7B) is taken along cross-sectional line 86-86 of FIG. 7A.
Figure 7B:
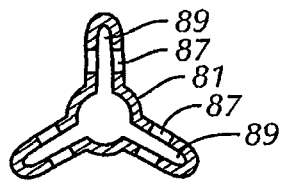

A side view of device 80 is shown in FIG. 7A. Device 80 includes body 81 with distal end 82, and fins 83. Body 81 and fins 83 have a lumen. Fins 83 include a plurality of openings 87 such that fluid can flow out of fins 83 through one or more openings 87. A cross-section of device 80 along line 86-86 in FIG. 7A is shown in FIG. 7B. FIG. 7B shows lumen 88 of body 81 in communication with lumen 89 of fins 83, and openings 87 positioned to allow for fluid flow out from fins 83 through the openings 87. The devices of the present invention can include two or more openings. In particular embodiments, each fin has 1 to 200 openings. In more particular embodiments, each fin has 20 to 120 openings. In even more particular embodiments, each fin has 40 to 80 openings. Distal end 82 may be opened or closed. Body 81 may be configured for passage of a guide wire, with a lumen that is separate from the lumen for infusion of fluid. In the embodiment shown in FIG. 6A, body 71 and/or fins 83 of device 80 are not able to expand. In other embodiments, body 81 and/or fins 83 are able to expand.

Figure 8:
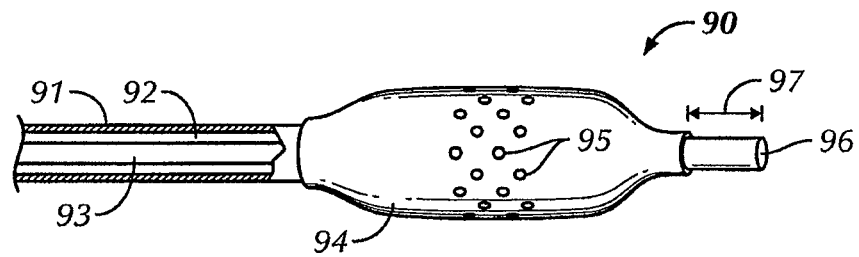
FIG. 8 shows a side view of one of the present medical devices, having a body and an expandable balloon coupled to the body, where the balloon has a plurality of openings to allow for passage of fluid from the balloon through the plurality of openings.
Figure 9A:
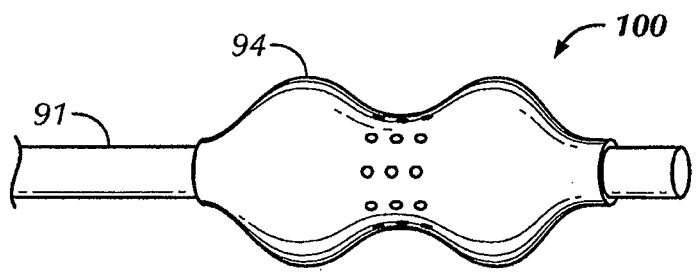
FIG. 9A-B: side views of the device of FIG. 8 after a first partial expansion (FIG. 9A) and in a fully expanded (FIG. 9B) position.
Figure 9B:
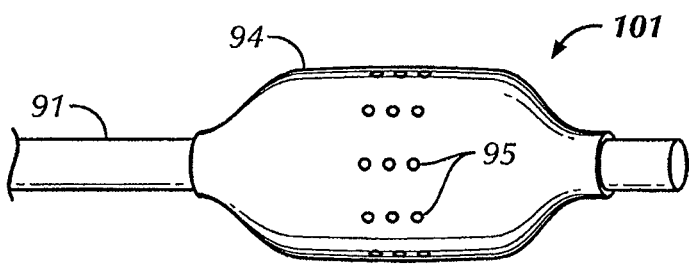

A further embodiment is device 90 shown in FIG. 8. Device 90 has a body 91 and a distal end 96, and an expandable balloon 94 coupled to body 91, balloon 94 having a plurality of openings, where balloon 94 is located at a distance 97 of more than 1 mm from distal end 96 of body. Device 90 includes body 91 that includes two lumens—a central lumen 93 for passage of a guidewire, and an annular lumen 92. Other embodiments include a single (nondivided) central lumen. Surrounding lumen 92 is in communication with balloon 94, such that fluid can be infused through surrounding lumen 92 of body 91 and pass out openings 95 of balloon 94. Device 90 includes distal end 96 that is open for passage of a guidewire. Annular lumen 92, in communication with the balloon, is not in communication with the distal end of body 91. Embodiments of the present devices may or may not include openings. In embodiments that do not include openings, the balloon is at least partially coated with a therapeutic agent. Some embodiments include a balloon with a plurality of openings, which is at least partially coated with a therapeutic agent. As depicted in FIG. 9A, 100 depicts balloon 94 after a first partial expansion. Balloon 94 can expand further by infusion of fluid through lumen of body 91 resulting in expansion of balloon 94, as depicted in FIG. 9B. Expansion of balloon 94 results in enlargement of openings 95 as a result of passage of fluid through the openings. A fully expanded balloon may have a diameter that is about the same as a conventional valvuloplasty balloon. In some embodiments, the diameter of an expanded balloon is about 2 cm to about 3 cm.

Figure 10A:
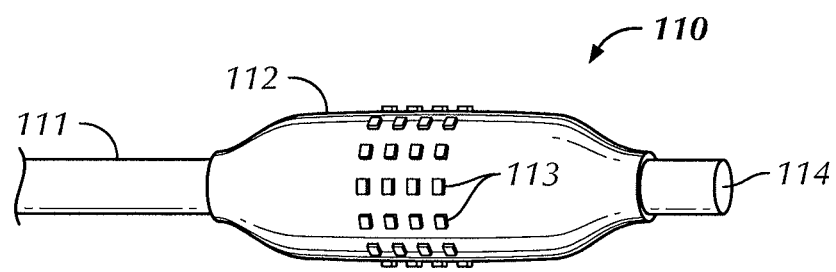
FIG. 10A-B: side views of one of the present medical devices, having a body and an expandable balloon coupled to the body, where the balloon has a plurality of nanofilaments attached to the balloon. The balloon is shown unexpanded (FIG. 10A) and expanded (FIG. 10B). A therapeutic agent may be attached to at least a portion of a nanofilament.

FIG. 10A depicts device 110 that includes a body 111 having a distal end 114, and an expandable balloon 112 coupled to body 111, the balloon having a plurality of nanofilaments 113, where the balloon is located at a distance 115 of more than 1 mm from distal end 114. The distance of the balloon from the distal end of the body can be any distance, so long as it is greater than a mm. In particular embodiments, the balloon is located between 2 mm to 20 cm from the distal end of the body. A "nanofilament" is defined to refer to a filament, fiber, or needle, less than 5 mm in length. In some embodiments, at least one nanofilament is at least partially coated with a therapeutic agent. Coating can be by any method known to those of ordinary skill in the art, as discussed above. In some embodiments, each nanofilament of the device is at least partially coated with a therapeutic agent. In further embodiments, at least one nanofilament is entirely coated with a therapeutic agent. In still further embodiments, all nanofilaments are entirely coated with a therapeutic agent. In some embodiments, body 111 has a lumen. The lumen may be a divided lumen to allow for passage of a guide wire and separate infusion of fluid, as discussed above. Infusion of fluid into lumen of body 111 may allow for expansion of balloon 112, thus facilitating greater contact of nanofilaments 113 with leaflets of a heart valve following positioning of the device such that balloon 112 is in contact with the valve.

Figure 10B:
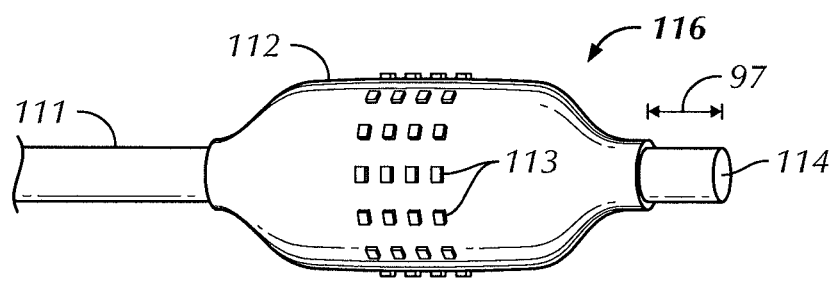

Nanofilaments may be composed of material such that they are designed to break off and become embedded in tissue such as valve leaflets. For example, the nanofilaments may be composed of a bioerodable therapeutic agent delivery matrix, as discussed above. In other embodiments, nanofilaments are not designed to break off, but therapeutic agent coated onto nanofilament is applied in a manner such that it would be expected to become released from the nanofilament upon contact with tissue, such as a cardiac valve. Inflation of the balloon such as depicted in FIG. 10B may facilitate contact of nanofilaments with valve leaflets to allow for maximal therapeutic agent release from nanofilaments. In some embodiments, the balloon includes one or more openings to provide for a communication with a lumen of the body of the device such that fluid can flow out of the balloon through the one or more openings.

In further embodiments, the nanofilaments are microneedles, wherein each microneedle has an opening that is designed for release of therapeutic agent from each microneedle. Infusion of a composition that includes one or more therapeutic agents through the device results in inflation of the balloon, and release of therapeutic agent-containing composition from each needle. Closure of valve leaflets combined with inflation of balloon brings valve leaflets in contact with microneedles, resulting in release of therapeutic agent into valve leaflets. In some embodiments, the microneedles are retractable.

Any method known to those of ordinary skill in the art can be applied in manufacturing the devices of the present invention. In some embodiments, for example, delivery members are separately manufactured from the body of the device, and then subsequently attached. For examples, attachment of delivery members to body may involve use of rings. In other embodiments, a body with attached delivery members is fabricated. Similarly, balloons can be fabricated separately or concurrently with the body of the devices set forth herein. In some examples, nanofilaments are attached to balloons using any method known to those of ordinary skill in the art. For example, nanofilaments can be applied to balloons using glue or adhesive. In other embodiments, nanofilaments are fabricated concurrently with the balloons of the present invention using technique known to those of ordinary skill in the art.

The devices set forth herein are composed of any material known to those of ordinary skill in the art. The device may be made of plastic, metal, or a combination of metal and plastic. For example, the materials may include, but are not limited to, one or more of latex, silicone, teflon, polyvinyl chloride (PVC), polyethylene (PE), polyolefin copolymer (POC), polyethylene terephthalate (PET), polyamid, polypyrrole, polyalanine, polyacetylene, polythiophene, polyvinylidene difluoride, polystyrene-polyisobutylene-polystyrene triblock copolymer (SIBS), polyethylene oxide, silicone rubber, mixtures, and block co-polymers thereof. Alternatively, the materials may include one or more metals or alloys in any number of configurations. For example, the materials may include stainless steel (e.g., 316L), titanium, or other medical grade alloys as are known, such as nickel-titanium alloys. These materials may also have a woven configuration or a solid extruded configuration. The device may be composed of a mixture of metal and plastic.

The selection of material allows the devices of the present invention to have the flexibility and the ability to be either pushed or pulled, thereby accomplishing the methods set forth in this application. As will be appreciated, selection of the material can be based generally on a broad range of technical properties, including, but not limited to, modulus of elasticity, flexural modulus, and Shore A hardness required for the embodiments of the present invention. In some embodiments, at least a portion of the device is self-expanding, and made of a suitable material such as nitinol or elgiloy. The delivery members may be deformable members or may be rigid.

The devices may be composed of one or more polymeric materials. Examples of polymeric materials suitably employed in the manufacture of the devices of the present invention include both non-elastomeric and elastomeric materials including, but not limited to, polyesters such as polyethyleneterephthalate, polyethers such as polyether-block-amides, polyether-polyesters and polyether/polyamide/polyesters, polyamides, nylons, polyurethanes including polyether urethanes, polyester urethanes and polyureas, polyolefins including low (LDPE) and high density polyethylene (HDPE), polypropylene and ethylene vinyl acetate copolymers, polymers of vinyl monomers such as polyvinylchlorides and vinylidene fluorides, fluoropolymers including PTFE, FEP, poly(meth)acrylates, polycarbonates, any copolymers thereof, and mixtures thereof.

Other examples include olefin polymers and copolymers, acrylic, styrenic and vinyl polymers (e.g. poly(vinyl chloride)) and copolymers; polyethers; polyurethanes; polyesters and copolyesters; polycarbonates; thermoplastic elastomers; silicone-polycarbonate copolymers; polyamides; thermoplastic polyimides; liquid crystal polymers; ABS (acrylonitrile butadiene styrene); ANS (acrylonitrile styrene); Delrin polyacetal; PEI (polyetherimide); polyetheretherketone (PEEK) and polyether sulfone (PES). Examples of olefin polymers and copolymers include irradiated polyethylene, polypropylene, ultra-high molecular weight polyolefins, low, linear low, medium and high density polyethylenes; polypropylenes; poly(ethylene vinyl acetate) (EVA); poly(ethylene vinyl alcohol) (EVOH) and EVA/EVOH terpolymers; ethylene-butylene-styrene block copolymers blended with low molecular weight polystyrene and, optionally, polypropylene, and similar compositions substituting butadiene or isoprene in place of the ethylene and butylene, and olefin ionomers (copolymers of olefin monomers and a metal salt of an olefinic acid, such as (meth)acrylic acid, succinic acid, maleic acid and fumaric acid).

Orientable polyesters, especially polyethylene terephthalate (PET), are among materials for forming catheter balloons. Suitable PET polymers have an initial intrinsic viscosity of at least 0.5, for instance, 0.6-1.3. Other high strength polyester materials, such as poly(ethylene napthalenedicarboxylate) (PEN), polytrimethylene terephthalate (PTT) and poly(butylene terephthalate) (PBT) may also be used. Polyester copolymers may also be employed, for instance, the random copolymers made from dimethyl terephthalate, dimethyl isophthalate and ethylene glycol described in U.S. Pat. No. 5,330,428.

Examples of polyamides which may be used include nylon 6, nylon 64, nylon 66, nylon 610, nylon 610, nylon 612, nylon 46, nylon 9, nylon 10, nylon II, nylon 12, and mixtures thereof.

The medical device article may be formed of polyurethanes such as Tecothane® from Thermedics. Tecothane® is a thermoplastic, aromatic, polyether polyurethane synthesized from methylene diisocyanate (MDI), polytetramethylene ether glycol (PTMEG) and 1,4 butanediol chain extender. Tecothane® 1065D and 1075D are examples. Other polyurethanes which have been used are Isoplast® 301, a high strength engineering thermoplastic polyurethane, and Pellethane® 2363-75D, both sold by Dow Chemical Co. References illustrating polyurethane balloon materials include U.S. Pat. No. 4,950,239, U.S. Pat. No. 5,500,180, U.S. Pat. No. 6,146,356, and U.S. Pat. No. 6,572,813. Devices of the invention may be also made of polyamide/polyether block copolymers. The polyamide/polyether block copolymers are commonly identified by the acronym PEBA (polyether block amide). The polyamide and polyether segments of these block copolymers may be linked through amide linkages, however, most preferred are ester linked segmented polymers, i.e. polyamide/polyether polyesters. Such polyamide/polyether/polyester block copolymers are made by a molten state polycondensation reaction of a dicarboxylic polyamide and a polyether diol. The result is a short chain polyester made up of blocks of polyamide and polyether.

It is also possible to utilize polyester/polyether segmented block copolymers and obtain balloon properties. Such polymers are made up of at least two polyester and at least two polyether segments. The polyester segments are polyesters of an aromatic dicarboxylic acid and a two to four carbon diol. The polyether segments of the polyester/polyether segmented block copolymers are aliphatic polyethers having at least 2 and no more than 10 linear saturated aliphatic carbon atoms between ether linkages. Examples of other polyethers which may be employed in place of the preferred tetramethylene ether segments include polyethylene glycol, polypropylene glycol, poly(pentamethylene ether) and poly(hexamethylene ether).

The polyester segments may be polyesters of an aromatic dicarboxylic acid and a two to four carbon diol. Suitable dicarboxylic acids used to prepare the polyester segments of the polyester/polyether block copolymers are ortho-, meta- or para-phthalic acid, napthalenedicarboxylic acid or meta-terphenyl-4,4'-dicarboxylic acids.

Balloons have been formed of a wide variety of homopolymer and copolymer materials. The strength characteristics of the balloon may be provided by a single polymer layer or by several layers of polymer material. Balloons with multiple structural polymer layers may be produced by coextrusion, as described in WO 92/19316, U.S. Pat. No. 5,270,086 and U.S. Pat. No. 5,290,306, or by a tube-in-tube technique as described in U.S. Pat. No. 5,512,051; and U.S. Pat. No. 5,587,125. In U.S. Pat. No. 5,270,086 it is proposed that a multilayer balloon could be made with an outer layer of a high tensile strength polymer and an inner bonding layer of a highly distensible polymer which had good melt bond and glue adhesion properties.

Polymer materials for forming medical devices are described in greater detail in U.S. Patent App. Pub. No. 20050142314, U.S. Pat. No. 7,026,026, U.S. Pat. No. 7,005,097, and U.S. Pat. No. 7,112,357, each of which is herein specifically incorporated by reference.

B. METHODS OF TREATMENT

1. Definitions a. Treatment and Prevention of Disease

"Treatment" and "treating" as used herein refer to administration or application of a therapeutic agent to a subject or performance of a procedure or modality on a subject for the purpose of obtaining a therapeutic benefit. A therapeutic benefit may be obtained by the reduction in the signs or symptoms of a disease or health-related condition, or by a physiological response that is intended to improve the health or well-being of a subject. For example, in the context of the present invention, a therapeutic benefit may be obtained by (1) reduction in the severity or frequency of clinical signs and symptoms of valvular disease, or (2) causing a physiological response, such as improved cardiac function or improved valvular function. Following treatment, signs and symptoms of a disease may or may not be reduced in frequency or severity. Treatment does not imply that the disease is necessarily cured, with complete resolution of signs and symptoms of disease. Nor does treatment require a measurable reduction in signs or symptoms of disease, or a measurable improvement in cardiac and/or valvular function. If a therapeutic agent was administered for the intended purpose of obtaining a therapeutic benefit, then a treatment was performed, regardless of whether there was any measurable improvement in disease symptoms or valve function.

Certain embodiments of the present invention pertain to methods of preventing valvular disease in a subject. "Prevention" and "preventing" are used according to their ordinary and plain meaning to mean "acting before" or such an act. In the context of a particular disease or health-related condition, those terms refer to administration or application of an agent, therapeutic agent, or remedy to a subject or performance of a procedure or modality on a subject for the purpose of blocking the onset of a disease or health-related condition. For example, a subject with disease in one heart valve may be at risk of developing disease in a second heart valve.

b. Diagnosis of Disease

"Diagnosing a disease" as used herein refer to the identification of the presence of a disease in a subject. For example, information from the results of a test, such as the results of a test that involve the administration of a diagnostic agent, can be examined by a skilled professional, and the presence or absence of disease determined.

c. Valvular Heart Disease

"Valvular disease" and "valvular heart disease" refer to any disease that can adversely affect the structure or function of a heart valve of a subject. In a human, for example, the heart valves include the aortic valve, mitral valve, pulmonic valve, and tricuspid valve. Major valvular heart diseases in humans include aortic stenosis, aortic insufficiency, mitral regurgitation, and mitral stenosis. In particular embodiments, the valvular disease is disease of the aortic valve.

d. Subject

"Subject" as used herein refers to any subject, such as a mammal. Examples of mammals include mice, rats, rabbits, dogs, cats, primates, and humans. In particular embodiments, the subject is a patient with known or suspected valvular disease. In particular embodiments, the subject is a patient with known or suspected aortic valvular disease.

2. Device Insertion

In addition to the devices discussed above, embodiments of the present invention concern methods for diagnosing or treating a valve disease in a subject that involve inserting any of the devices set forth above in a blood vessel of the subject, where at least a portion of at least one delivery member of the device is coated with a therapeutic agent, and positioning the device such that the valve leaflets of the valve are in contact with that delivery member, where contact results in delivery of therapeutic agent to the valve and diagnosis or treatment of the valve disease.

The valvular disease can be any disease as discussed above, but in particular embodiments the valvular disease is aortic valvular disease, such as aortic stenosis, aortic regurgitation (insufficiency), or atresia of the aortic valve. The therapeutic agent can be any of those therapeutic agents discussed above, but in particular embodiments, the therapeutic agent is rapamycin, paclitaxel, sirolimus, or a nitric oxide-enhancing agent.

Insertion of the device can be by any method known to those of ordinary skill in the art. For example, the device may be inserted into the femoral artery and advanced such that the distal end of the device is positioned in the left ventricle of the subject. Positioning of the device may be monitored using any imaging modality known to those of ordinary skill in the art, such as fluoroscopy. The device may include a radiopaque marker to mark a part of the device, such as the distal end of the device. Radiopaque markers allow for visualization of the location and position of parts of device, such as under fluoroscopy. The radiopaque material can be any such material known to those of ordinary skill in the art. Examples include, but are not limited to, gold, tantalum, and platinum.

In some embodiments, the device is passed over a guide wire. One of ordinary skill in the art would be familiar with use of guide wires for positioning of devices that are inserted into the vasculature of the subject.

Figure 11A:
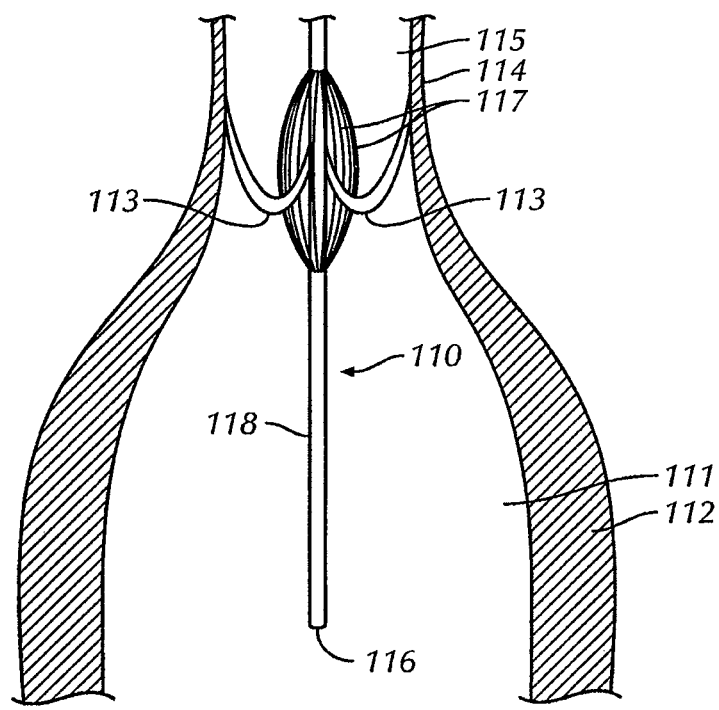
FIGS. 11A-B: a side view of one of the present medical devices positioned for delivery of a therapeutic agent to the aortic valve of a patient.
Figure 11B:
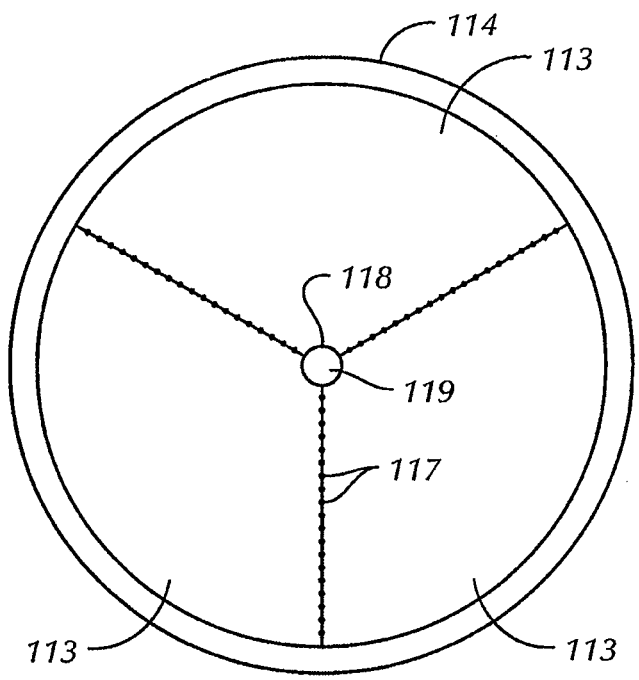

FIG. 11A depicts device 110 in proper position for treatment of aortic valve disease in a patient. Regarding anatomic detail, 111 is the chamber of the left ventricle, 112 is the wall of the left ventricle, 113 shows aortic valve leaflets, 114 is the wall of the ascending aorta, and 115 is the lumen of the ascending aorta. Device 110 has been advanced over a guidewire from the point of insertion in the femoral artery. Distal end 116 of body 118 of device 110 is positioned within chamber 111 of the left ventricle, such that delivery members 117 are in contact with aortic valve leaflets 113 when the valve leaflets are in the closed position, as shown in FIG. 11A. The guide wire is then removed. In the embodiment show, device 110 includes 40 delivery members.

FIG. 11B depicts magnified cross-sectional view from lumen of ascending aorta looking down onto the aortic valve when the valve leaflets are in the closed position following positioning of device 110. As shown in FIG. 11B, delivery members are configured such that they are in contact with a valve leaflet of a heart of a subject when the body of the device is passed across a valve of the heart when the valve leaflets are in a closed or substantially closed position. Delivery members 117 are in contact with valve leaflets 113. Shown is lumen 119 of device 110 for passage of a guide wire. Upon contact with valve leaflets, the therapeutic agent that is coated on a given delivery member makes contact with a valve leaflet. The mechanical process of valve closure, with the resulting contact of delivery members with valve leaflets, results in the release of therapeutic agent from some delivery members. The therapeutic agent may become attached to the valve leaflet, or more be released into the circulation of the subject, resulting in an increase in the bioavailability of the therapeutic agent at the site of disease (aortic valves). Release may be initiated, for example, by exposure of the therapeutic agent or device to a particular pH, such as physiological pH, or by infusion of fluid through the lumen of the device. In some embodiments, the coating is designed for controlled release, such as release facilitated by an increase in temperature relative to ambient room temperature. FIG. 11B shows that when valve leaflets are in a closed or substantially closed position, delivery members become configured such that they are spaced at varying distances along the valve commissures as a result of pressure from the valve leaflets due to closure of the valve.

Figure 12A:
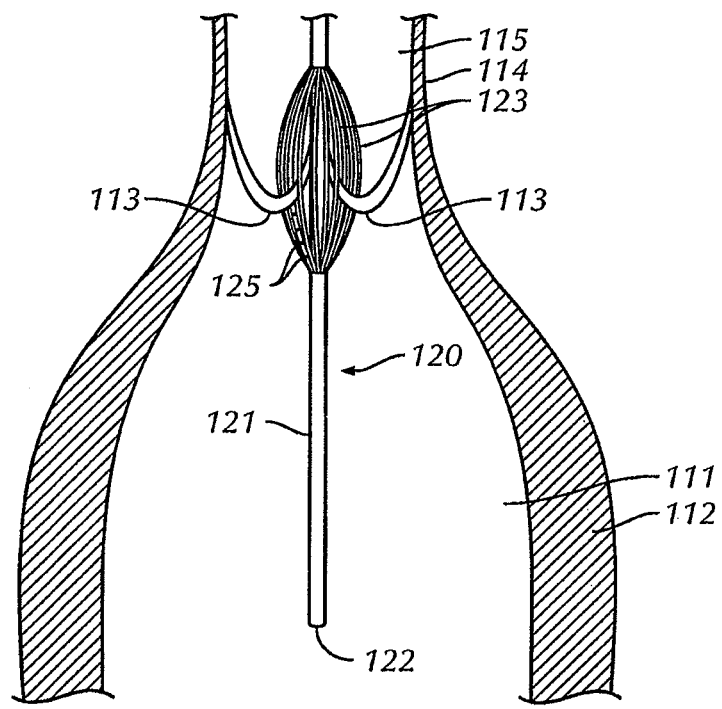
FIGS. 12A-B: a side view of one of the present medical devices positioned for delivery of a therapeutic agent to the aortic valve of a patient.
Figure 12B:
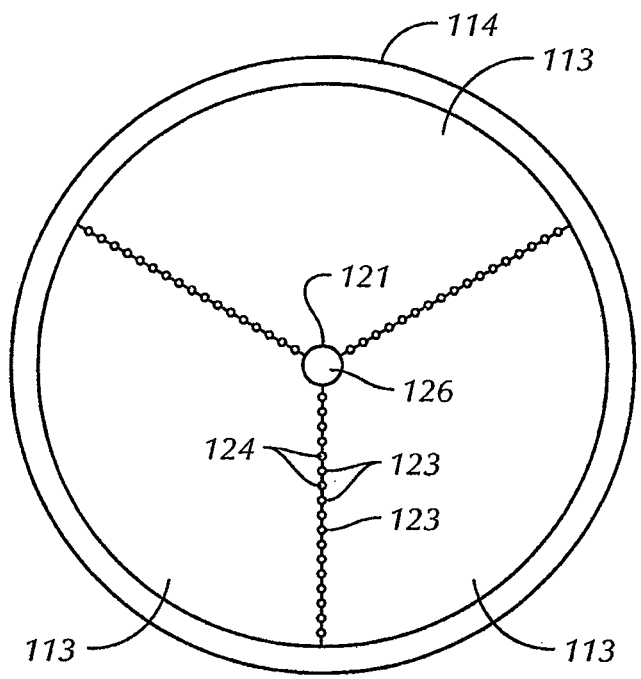

FIG. 12A depicts side view showing positioning of device 120 for treatment of aortic valve disease in a patient. Distal end 122 of device 120 is positioned within left ventricle 111. Each delivery member 123 includes a lumen and a plurality of openings 125 in communication with that lumen such that fluid can flow out of that delivery member through the one or more openings. Body 121 of device 120 includes a lumen in direct communication with the lumen of each delivery member, such that fluid can flow from body. FIG. 12B depicts magnified cross-sectional view from lumen of ascending aorta looking down onto the aortic valve when the valve leaflets are in the closed position following positioning of device 120. As shown in FIG. 12B, delivery members are configured such that they are in contact with a valve leaflet of a heart of a subject when the body of the device is passed across a valve of the heart when the valve leaflets are in a closed or substantially closed position. FIG. 12B shows that when valve leaflets are in a closed or substantially closed position, delivery members become configured such that they are spaced at varying distances along the valve commissures as a result of pressure from the valve leaflets due to closure of the valve.

As can be seen in FIG. 12B, delivery members 123 are in contact with valve leaflets 113. Contact between valve leaflets 113 and delivery members 123 is expected to be maximal when valve leaflets 113 are in the closed position, as shown in FIG. 12B. Delivery members 123 include lumens. Body 121 of device 120 includes central lumen 126. Once properly positioned, a pharmaceutical composition that includes one or more therapeutic agents and a carrier can be infused through lumen 126 of body 121 of device, such that the composition can be released from the delivery members 123 and contacted with the valve leaflets 113. The openings in the delivery members may be small enough to only allow for a slight weeping of pharmaceutical composition, or they might be of a size that would allow more rapid infusion or a greater volume of infusate to be delivered to the aortic valve leaflets. The openings in the delivery members can be of any size, but in particular embodiments, they have a diameter of about 0.1 mm, about 0.2 mm, about 0.3 mm, about 0.4 mm, about 0.5 mm, about 0.6 mm, about 0.7 mm, about 0.8 mm, about 0.9 mm, about 1.0 mm, about 1.2 mm, about 1.4 mm, about 1.6 mm, about 1.8 mm, about 2.0 mm, or greater.

Infusion of the pharmaceutical composition through the device can be timed with the cardiac cycle. Timing of infusion of the pharmaceutical composition through the device can be by any method known to those of ordinary skill in the art. For example, U.S. Patent App. Pub. No. 20070005011, specifically incorporated by references, teaches devices and methods for delivery of therapeutic agents through catheters that can be timed, such as timed to the cardiac cycle. For example, delivery may be timed to occur with rapid pacing of the heart, may be in short bursts, or may be by continuous infusion over a course of minutes to hours.

Figure 13A:
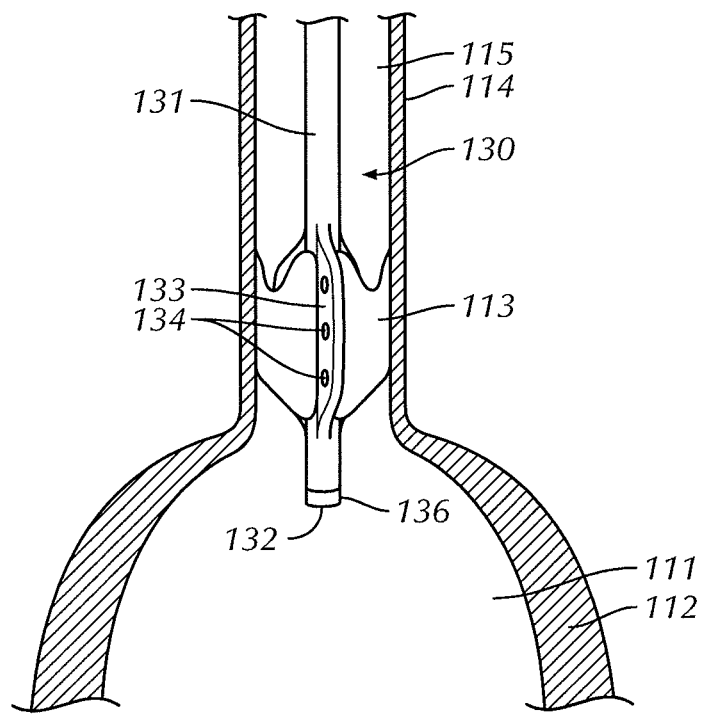
FIGS. 13A-B: a side view of one of the present medical devices positioned for delivery of a therapeutic agent to the aortic valve of a patient. The device includes a body with distal end and three fins longitudinally oriented along a portion of the body.
Figure 13B:
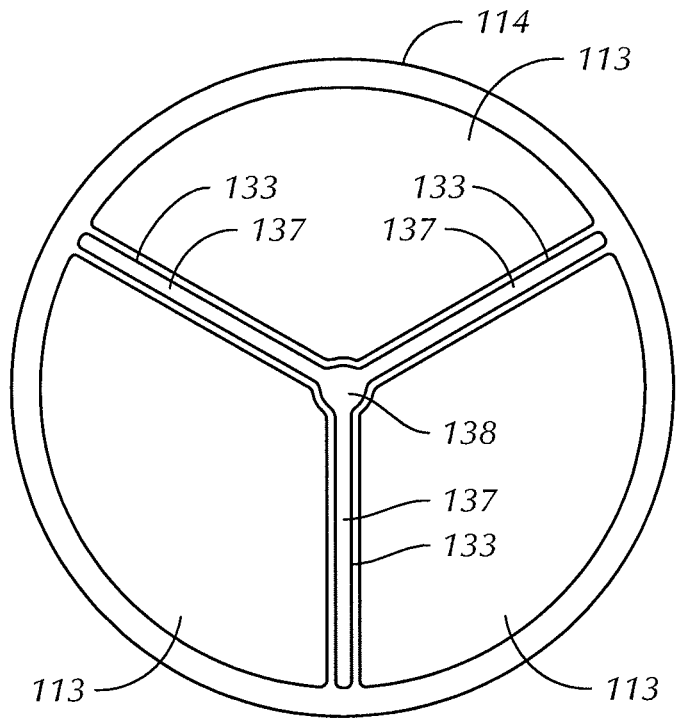

FIG. 13A shows device 130 properly positioned for delivery of a therapeutic agent to the aortic valve of a subject. Distal end 132 includes radiopaque marker 136 to facilitate placement of distal end 132 in left ventricle 111. Device 130 includes body 131 and three fins 133. Fins 133 include a plurality of openings 134. Positioning of the device involves placing the device such that fins 133 are located within commissures of aortic valve leaflets 113. FIG. 13B depicts magnified cross-sectional view from lumen of ascending aorta looking down onto the aortic valve when the valve leaflets are in the closed position following positioning of device 130. As shown in FIG. 13B, the fins are configured such that they are in contact with a valve leaflet of a heart of a subject when the body of the device is passed across a valve of the heart when the valve leaflets are in a closed or substantially closed position.

Device 130 includes body 131 having a lumen 138 in communication with lumen of fins 137, such that fluid that is infused through lumen of device 130 can flow out of the delivery member through the openings 134. In some embodiments, at least one fin is at least partially coated with a drug. In other embodiments, the fins of the device do not include a plurality of openings, but are at least partially coated with a drug. Release of the drug from the fins is facilitated by contact of valve leaflets with the device and the positioning of fins within commissures of aortic valve leaflets.

Figure 14:
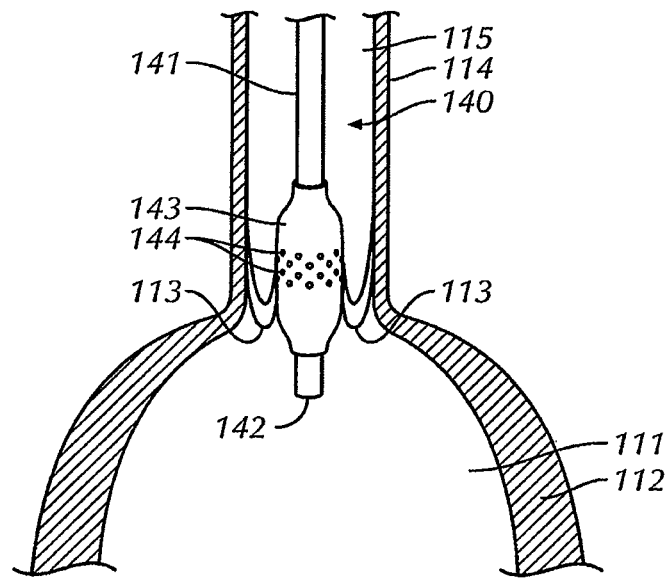
FIG. 14 shows a side view of one of the present medical devices positioned for delivery of a therapeutic agent to the aortic valve of a patient. The device includes a body with an expandable balloon connected to the body, where the balloon includes a plurality of openings to allow for passage of fluid from the balloon through the openings.

FIG. 14 shows a side view of device 140 properly positioned for delivery of a therapeutic agent to the aortic valve of a subject. Distal end 142 of device 140 is positioned within left ventricle 111. Device 140 includes body 141 with expandable balloon coupled to body 141. Body 141 of device 140 includes a central lumen, such that a pharmaceutical composition that includes a therapeutic agent that is infused into the lumen can flow out of the balloon through the one or more openings. In this manner, therapeutic agent that is released from the device is contacted with the valve leaflets. Delivery of a therapeutic agent through the device can be timed to the cardiac cycle, using any manner known to those of ordinary skill in the art, as discussed above.

Figure 15:
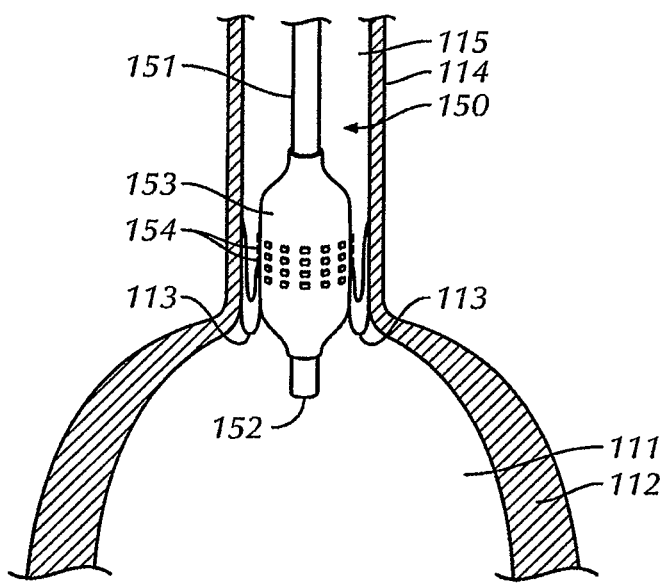
FIG. 15 shows a side view of one of the present medical devices positioned for delivery of a therapeutic agent to the aortic valve of a patient. The device includes a body with an expandable balloon connected to the body, where the balloon includes a plurality of nanofilaments coated with a therapeutic agent. Expansion of the balloon, as shown, facilitates contact of the aortic valve leaflets with the nanofilaments, and delivery of therapeutic agent to the aortic valve leaflets.

FIG. 15 depicts a side view of device 150 properly positioned for delivery of a therapeutic agent to the aortic valve of a subject. Distal end 152 of device 150 is positioned within left ventricle 111, such that balloon 153 is in contact with valve leaflets 113. Balloon 153 includes a plurality of therapeutic agent-coated nanofilaments 154. FIG. 15 depicts balloon in expanded position, which results in increased contact between nanofilaments 154 and leaflets of aortic valves 113. Contact between nanofilaments 154 and valve leaflets 113 result in release of therapeutic agent from nanofilaments, and contact of therapeutic agent with surface of valve leaflets. As with other embodiments, delivery of a therapeutic agent using the device can be timed to the cardiac cycle, using any manner known to those of ordinary skill in the art, as discussed above. Inflation of the balloon, for example, can be timed to correspond to the period when the left ventricle is not contracting. Further, the device can be designed such that it is of a sufficient size to not significantly disrupt flow of blood across the valve surface during the period of left ventricular contraction.

The present medical devices can be left in place for any duration of time as is clinically necessary. Duration of treatment depends on a number of factors, including patient-specific factors such as the nature and severity of the valve disease, age, underlying health factors, and other factors such as the specific device being utilized and the therapeutic agent. For example, infusion of a pharmaceutical composition containing one or more therapeutic agents may take place over 30 seconds to one hour. Regarding devices that are coated with a therapeutic agent, the device can be left in position and monitored in a subject for a period of from about 30 seconds to about 1 day.

In some embodiments, treatment can be repeated once, or more than once. The decision as to retreatment is determined based on factors such as initial response to therapy, nature of the disease, and patient-specific factors. One of ordinary skill in the art would be able to assess such factors to determine if and when repeat therapy would be indicated. In some of the embodiments set forth herein, the method further includes identifying a subject in need of treatment. For example, identifying such a subject may be based on clinical factors such as severity of disease or failed response to conventional medical therapy. Further, as discussed in greater detail below, some embodiments of the present methods include the administration of one or more secondary forms of therapy of valvular disease.

3. Infusions

The phrase "pharmaceutical composition" refers to molecular compositions that do not produce an adverse, allergic or other untoward reaction when administered to a mammal or human, as appropriate. As used herein, a "pharmaceutical composition" includes any and all solvents, dispersion media, coatings, antibacterial and antifungal agents, isotonic and absorption delaying agents and the like. The phrase "pharmaceutically effective" refers to that amount of a particular composition that is known or suspected to be of benefit in diagnosing, treating, or preventing a disease in a subject.

Infusions can be provided over any duration of time as determined by one of ordinary skill in the art. For example, infusions may be provided over about 1 minute, about 2 minutes, about 5 minutes, over about 10 minutes, over about 15 minutes, over about 20 minutes, over about 30 minutes, over about 1 hour, and so forth. The administration could be intra-operative or post-operative.

C. METHODS OF INSTRUCTION

A further embodiment of the present invention pertains to a method of instructing a person to perform a procedure, comprising providing the person with a computer readable media containing machine-readable instructions that, when executed using a computer, cause the display of a real or virtual procedure of delivering a therapeutic agent to a heart valve using any of the aforementioned devices or catheters, where the procedure comprises the steps of inserting the device or catheter in a blood vessel of the subject, and positioning the device or catheter such that the valve leaflets of the valve are in contact with the device or catheter. In particular embodiments, the heart valve is the aortic valve of a subject. The therapeutic agent can be any of those drugs discussed above. In particular embodiments, the therapeutic agent is rapamycin, paclitaxel, sirolimus, or a nitric oxide-enhancing agent. In a particular embodiment, the computer readable media is a CD or DVD.

D. KITS

Certain embodiments of the present invention are generally concerned with kits. For example, in some embodiments the kit includes one or more of the medical devices of the present invention and at least one sealed container. In embodiments where the kit includes more than one medical device of the present invention, the devices may be packaged separately in sealed containers. The kit may include instructions for insertion of the device. In embodiments where the device is designed with a lumen for infusion of a fluid, the kit may further include at least one sealed container that includes a composition comprising a pharmaceutically acceptable carrier for infusion though the catheter. In some embodiments, the composition includes one or more therapeutic agents. The therapeutic agents can be any of those therapeutic agents discussed above.

E. DIAGNOSTIC AGENTS AND IMAGING

In some embodiments of the present invention, the therapeutic agent is a diagnostic agent. In some embodiments, the diagnostic agent is an agent from which a signal can be detected. Thus, some embodiments of the present methods may further involve detecting a signal from the therapeutic agent composition that has been infused through the device. Most preferably, the signal that is detected is signal from diagnostic agent that is infused in the region of the valve of interest in the subject. The diagnostic agent can be an imaging agent, such as an imaging agent that can be imaged using CT, MRI, gamma camera, PET, SPECT, ultrasound, or optical imaging. In particular embodiments, the diagnostic agent is a radionuclide. For example, the delivery of the therapeutic agent could be combined with imaging, such that drug release can be imaged. For example, therapeutic agent may be delivered in a nanoparticle comprised of a lipid and a perfluorocarbon.

F. COMBINATION THERAPY

Some embodiments of the invention pertain to methods of treating valvular disease in a subject using any of the devices set forth in this application, where one or more secondary forms of therapy of valvular heart disease are administered to the subject.

The secondary form of therapy can be any type of therapy for valvular heart disease known to those of ordinary skill in the art. In particular embodiments, the secondary form of therapy involves administration of one or more additional pharmacologic therapies using conventional methods of administration. Therapy can involve administration of any pharmacological agent, examples of which have been set forth elsewhere in this specification. For example, administration may be oral administration or intravenous administration. Other examples of therapies for valvular disease include valvuloplasty and surgical therapy of a heart valve.

Administration of the compositions of the present invention to a patient will follow general protocols for the administration of therapeutic agent therapy, taking into account the toxicity, if any, of these agents. It is expected that treatment may be repeated as necessary.

G. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Demonstration of Local Valve Delivery

A study was conducted to demonstrate local valve delivery of a reporter agent.

The study utilized explanted rat and rabbit hearts. The device, which was similar to device 90 shown in FIG. 8, included microporous balloons of various diameters that fit the anatomy of the particular animal (e.g., 3.0 mm diameter, 4.0 mm diameter). A deflated microporous balloon was placed across the aortic valve. The balloon was inflated by infusing a 1% solution of Evan's blue such that the sides of the balloon contacted the valve opening, to visualize delivery of an agent to the valve area. The infusion was time-varied. Times tested were 5 sec to 1 min. All specimens showed that the solution leaked out of the balloon through micropores and stained valve leaflets, even in the presence of a continuous saline flush mimicking cardiac blood flow through the left atrium.

Those of skill in the art will appreciate that, in the detailed description above, certain well-known components and assembly techniques have been omitted so that the present medical devices and methods are not obscured in unnecessary detail. Dimensions provided in English units may be translated to the corresponding metric unit by rounding to the nearest millimeter.

All the disclosed embodiments of the invention can be made and used without undue experimentation in light of the disclosure. The individual medical devices described above need not be made in the exact disclosed forms, or combined in the exact disclosed configurations, but could be provided in any suitable form, and/or combined in any suitable configuration consistent with the claims below. Further, although the present methods can be practiced using the specific disclosed elements, such methods can also be practiced incorporating other elements or techniques consistent with the claims below.

References

The following references, to the extent that they provide exemplary procedural or other details supplementary to those set forth herein, are specifically incorporated herein by reference.

U.S. Pat. No. 4,950,239
U.S. Pat. No. 5,270,086
U.S. Pat. No. 5,290,306
U.S. Pat. No. 5,330,428
U.S. Pat. No. 5,500,180
U.S. Pat. No. 5,512,051
U.S. Pat. No. 5,587,125
U.S. Pat. No. 5,591,227
U.S. Pat. No. 5,733,327
U.S. Pat. No. 5,899,935
U.S. Pat. No. 6,146,356
U.S. Pat. No. 6,364,856
U.S. Pat. No. 6,403,635
U.S. Pat. No. 6,425,881
U.S. Pat. No. 6,572,813
U.S. Pat. No. 6,716,242
U.S. Pat. No. 6,918,929
U.S. Pat. No. 6,939,376
U.S. Pat. No. 7,005,097
U.S. Pat. No. 7,026,026
U.S. Pat. No. 7,112,357
U.S. Patent Appln. 2005/0075662
U.S. Patent Appln. 20050142314
U.S. Patent Appln. 2006/0229659
U.S. Patent Appln. 20070005011
Henson et al., *AJNR Am. J. Neuroradiol.*, 25(6):969-972, 2004.
Strunk and Schild, *Eur. Radiol.*, 14(6):1055-1062, 2004.
PCT Appln. WO 92/19316

What is claimed is:

1. A method for diagnosing or treating a heart valve disease in a subject, comprising:
   a) using a device comprising:
      an elongate body having a distal end and a longitudinal axis; and
      a plurality of delivery members coupled to the elongate body, where each member has a first end, a middle portion, and a second end, and the first and second ends of at least one of the delivery members are coupled to the elongate body at locations that are proximal to the distal end of the elongate body, wherein at least one of the delivery members has a lumen and one or more openings in communication with that lumen;
   b) inserting the device into the subject's blood vessel;
   c) positioning the device inside the subject's heart such that a delivery member contacts a heart valve; and d) applying a therapeutic agent to the heart valve by flowing the therapeutic agent out from the one or more openings of the delivery member having the lumen.

2. The method of claim 1, where the therapeutic agent is rapamycin, paclitaxel, sirolimus, a nitric oxide-enhancing agent, a statin, an angiotensin converting enzyme (ACE) inhibitor, a PPAR agonist, an anti-inflammatory agent, an anti-stenotic agent, an antibiotic, atorvastatin, or quinapril.

3. The method of claim 1, wherein each delivery member is 1-20 cm in length.

4. The method of claim 1, wherein the distance between the distal end of the catheter and the distal-most coupling location of each of the delivery members to the elongate body is 1-15 cm.

5. The method of claim 1, where at least one delivery member is at least partially coated with the therapeutic agent.

6. The method of claim 5, where the therapeutic agent is rapamycin, paclitaxel, sirolimus, a nitric oxide-enhancing agent, a statin, an angiotensin converting enzyme (ACE) inhibitor, a PPAR agonist, an anti-inflammatory agent, an anti-stenotic agent, an antibiotic, atorvastatin, or quinapril.

\* \* \* \* \*